(12) United States Patent
Eggenweiler et al.

(10) Patent No.: US 7,141,572 B2
(45) Date of Patent: Nov. 28, 2006

(54) HYDRAZONO-MALONITRILES

(75) Inventors: Hans-Michael Eggenweiler, Darmstadt (DE); Michael Wolf, Darmstadt (DE); Norbert Beier, Reinheim (DE); Pierre Schelling, Muehltal (DE); Thomas Ehring, Remscheid (DE)

(73) Assignee: Merck Patent Gesellschaft, Darmstadt (DE)

( * ) Notice: Subject to any disclaimer, the term of this patent is extended or adjusted under 35 U.S.C. 154(b) by 148 days.

(21) Appl. No.: 10/494,631

(22) PCT Filed: Oct. 10, 2002

(86) PCT No.: PCT/EP02/11351

§ 371 (c)(1),
(2), (4) Date: May 4, 2004

(87) PCT Pub. No.: WO03/039548

PCT Pub. Date: May 15, 2003

(65) Prior Publication Data

US 2004/0261190 A1  Dec. 30, 2004

(30) Foreign Application Priority Data

Nov. 5, 2001  (EP) ................... 01125455

(51) Int. Cl.
*C07D 403/12* (2006.01)
*C07D 237/04* (2006.01)
*A61K 31/501* (2006.01)
*A61K 31/50* (2006.01)
*A61P 11/06* (2006.01)

(52) U.S. Cl. ...................... 514/247; 544/224; 544/238; 514/252.07; 206/570

(58) Field of Classification Search ................ 544/224, 544/238; 514/247, 252.05; 206/570
See application file for complete search history.

(56) References Cited

FOREIGN PATENT DOCUMENTS

| WO | 98 06704 | 2/1998 |
|---|---|---|
| WO | 99 65880 | 12/1999 |
| WO | 00 26201 | 5/2000 |
| WO | 01 04099 | 1/2001 |

OTHER PUBLICATIONS

Hungarian Abstract P0001760 (May 28, 2001).

*Primary Examiner*—Kahsay Habte
(74) *Attorney, Agent, or Firm*—Millen, White, Zelano & Branigan, P.C.

(57) ABSTRACT

Hydrazono-malonitrile derivatives of the formula (I) in which $R^1$, $R^2$, $R^3$, $R^{3'}$ and $R^4$ have the meanings given in Claim 1 act as phosphodiesterase IV inhibitors and can be employed for the treatment of osteoporosis, tumours, cachexia, atherosclerosis, rheumatoid arthritis, multiple sclerosis, diabetes mellitus, inflammatory processes, allergies, asthma, autoimmune diseases, myocardial diseases and AIDS (I)

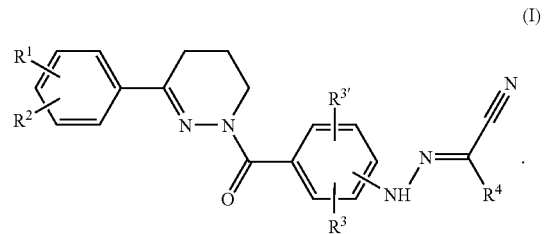

12 Claims, No Drawings

HYDRAZONO-MALONITRILES

The invention relates to compounds of the formula I

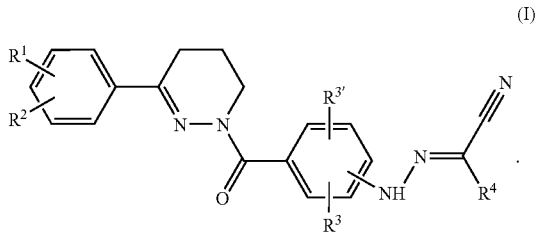

(I)

in which

R$^1$, R$^2$ in each case independently of one another are H, OH, OR$^5$, —SR$^5$, —SOR$^5$, —SO$_2$R$^5$ or Hal, R$^1$ and R$^2$ together are also —OCH$_2$O— or —OCH$_2$CH$_2$O—, R$^3$, R$^{3'}$ in each case independently of one another are H, R$^5$, OH, OR$^5$, NH$_2$, NHR$^5$, NAA', NHCOR$^5$, NHCOOR$^5$, Hal, COOH, COOR$^5$, CONH$_2$, CONHR$^5$ or CONR$^5$A', R$^4$ is CN or

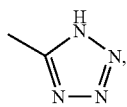

R$^5$ is A or cycloalkyl with 3 to 6 C-atoms, which can be substituted by 1 to 5 F and/or Cl atoms, or —(CH$_2$)$_n$—Ar, A, A' in each case independently of one another are alkyl with 1 to 10 C-atoms or are alkenyl with 2 to 8 C-atoms, which can be substituted by 1 to 5 F and/or Cl atoms, A and A' together are also cycloalkyl or cycloalkylene with 3 to 7 C-atoms, wherein one CH$_2$ group can be replaced by O, NH, NA, NCOA or NCOOA, Ar is phenyl, n is 0, 1 or 2, Hal is F, Cl, Br or I and their pharmaceutically usable derivatives, solvates and stereo-isomers, including mixtures thereof in all ratios.

1-Benzoyltetrahydropyridazines have been described as progesterone receptor ligands, for example in J. Med. Chem. 38, 4878 (1995). Other arylalkanoylpyridazines are disclosed, for example, in EP 0 922 036, EP 1 124 809 or WO 01/04099.

The invention was based on the object of finding novel compounds having valuable properties, in particular those which can be used for the production of medicaments.

It has been found that the compounds of the formula I and their salts and solvates have very valuable pharmacological properties together with good tolerability.

The compounds of formula I show a selective inhibition of phosphodiesterase IV, which is associated with an intracellular increase in cAMP (N. Sommer et al., Nature Medicine, 1, 244–248 (1995)). The inhibition of PDE IV can be demonstrated, for example, analogously to C. W. Davis in Biochim. Biophys. Acta 797, 354–362 (1984).

The affinity of the compounds of the invention for phosphodiesterase IV is measured by determining their IC$_{50}$ values (the concentration of inhibitor required to achieve 50% inhibition of the enzyme activity).

The compounds according to the invention can be employed for the treatment of asthmatic disorders. The antiasthmatic action of the PDE IV inhibitors is described, for example, by T. J. Torphy et al. in Thorax, 46, 512–523 (1991) and can be determined, for example, by the method of T. Olsson, Acta allergologica 26, 438–447 (1971).

Since cAMP inhibits osteoclastic cells and stimulates osteogenetic cells (S. Kasugai et al., M 681 and K. Miyamoto, M 682, in Abstracts of the American Society for Bone and Mineral Research 18th Annual Meeting, 1996), the compounds according to the invention can be employed for the treatment of osteoporosis.

The compounds moreover show an antagonistic action on the production of TNF (Tumour Necrosis Factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The anti-inflammatory action of the substances according to the invention and their efficacy for the treatment of, for example, autoimmune disorders such as multiple sclerosis or rheumatoid arthritis can be determined analogously to the methods of N. Sommer et al., Nature Medicine 1, 244–248 (1995) or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 236ff. (1995); J. M. Argiles et al., Med. Res. Rev. 17, 477ff. (1997)).

PDE IV inhibitors can also inhibit the growth of tumour cells and are therefore suitable for tumour therapy (D. Marko et al., Cell Biochem.

Biophys. 28, 75ff. (1998)). The action of PDE IV inhibitors in tumour treatment is described, for example, in WO 95 35 281, WO 95 17 399 or WO 96 00 215.

PDE IV inhibitors can prevent mortality in models of sepsis and are therefore suitable for the therapy of sepsis (W. Fischer et al., Biochem. Pharmacol. 45, 2399ff. (1993)).

They can furthermore be employed for the treatment of memory disorders, atherosclerosis, atopic dermatitis and AIDS.

The action of PDE IV inhibitors in the treatment of asthma, inflammatory disorders, diabetes mellitus, atopic dermatitis, psoriasis, AIDS, cachexia, tumour growth or tumour metastases is described, for example, in EP 77 92 91.

The compounds of the formula I can be employed as pharmaceutical active compounds in human and veterinary medicine. They can furthermore be employed as intermediates for the preparation of further pharmaceutical active compounds.

Furthermore, the invention relates to the use of type 4 phosphodiesterase inhibitors (PDE IV inhibitors) of formula I to treat diseases and relates to combinations of compounds of formula I with other drugs.

Reference is made to WO 01/57025 which discloses special pyrimidine derivatives as PDE IV inhibitors, their use for treating diseases and combinations with other drugs.

Accordingly, the invention provides in particular for the use of compounds of formula I and their physiologically acceptable salts and solvates for preparing a medicament for treating a subject suffering from a disease or condition mediated by the PDE4 isozyme in its role of regulating the activation and degranulation of human eosinophils.

WO 01/57025 discloses various in vitro assays and animal model experiments, which are capable of providing data sufficient to define and demonstrate the therapeutic utility of compounds of formula 1.

Compounds of formula I inhibit the PDE4 isozyme and thereby have a wide range of therapeutic applications, because of the essential role which the PDE4 family of isozymes plays in the physiology of all mammals. The enzymatic role performed by the PDE4 isozymes is the intracellular hydrolysis of adenosine 3', 5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP elevation, include inhibition of superoxide production, degranulation, chemotaxis and tumor necrosis factor (TNF) release in eosinophils, neutrophils and monocytes.

The invention accordingly relates to the compounds of the formula I and to a process for the preparation of compounds of the formula I, wherein $R^4$ is cyano, and of their salts and solvates, characterized in that
a) a compound of the formula II

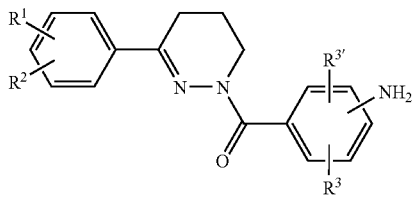

in which
$R^1$, $R^2$, $R^3$, $R^{3'}$ have the meanings indicated in claim 1, is reacted with malodinitrile, or
b) in a compound of the formula I, a radical $R^4$ is converted into another radical $R^4$ by converting a cyano group to a tetrazole group, and/or in that a basic compound of the formula I is converted into one of its salts by treatment with an acid.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean, for example, compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61–67 (1995).

For all radicals which occur more than once, their meanings are independent of one another.

Above and below, the radicals $R^1$, $R^2$, $R^3$, $R^{3'}$, $R^4$, $R^5$, A, A' and L have the meanings indicated in the formulae I, I-I, II, III, IV, if not expressly stated otherwise.

A is preferably alkyl, furthermore alkyl preferably substituted by 1 to 5 fluorine and/or chlorine atoms, furthermore preferably alkenyl.

In the above formulae, alkyl is preferably unbranched and has 1, 2, 3, 4, 5, 6, 7, 8, 9 or 10 C atoms, preferably 1, 2, 3, 4, 5 or 6 C atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Methyl, ethyl, trifluoromethyl, propyl, isopropyl, butyl, n-pentyl, n-hexyl or n-decyl is particularly preferred.

Cycloalkyl preferably has 3–7 C atoms and is preferably cyclopropyl or cyclobutyl, furthermore preferably cyclopentyl or cyclohexyl, and further also cycloheptyl; cyclopentyl is particularly preferred.

Alkenyl is preferably allyl, 2- or 3-butenyl, isobutenyl, sec-butenyl; 4-pentenyl, isopentenyl or 5-hexenyl is further preferred.

Alkylene is preferably unbranched and is preferably methylene or ethylene, and further preferably propylene or butylene.

A' is preferably methyl, ethyl, propyl or butyl.

Hal is preferably F, Cl or Br, but also I.

The radicals $R^1$ and $R^2$ can be identical or different and are preferably in the 3- or 4-position of the phenyl ring. They are, for example, independently of one another H, hydroxyl, —S—$CH_3$, —SO—$CH_3$, —$SO_2CH_3$, F, Cl, Br or I or together methylenedioxy. Preferably, however, they are each methyl, ethyl, propyl, methoxy, ethoxy, propoxy, isopropoxy, benzyloxy, or else fluoro-, difluoro- or trifluoromethoxy, or 1-fluoro-, 2-fluoro-, 1,2-difluoro-, 2,2-difluoro-, 1,2,2-trifluoro- or 2,2,2-trifluoro-ethoxy.

$R^1$ is particularly preferably ethoxy, benzyloxy, F, propoxy, or isopropoxy, furthermore, difluormethoxy; or cycloalkoxy, e.g. cyclopentoxy.

$R^2$ is particularly preferably methoxy, ethoxy, F or ethyl, furthermore, difluormethoxy; or cycloalkoxy, e.g. cyclopentoxy.

$R^3$ is preferably H, methyl, ethyl, propyl, isopropyl, butyl, tert.-butyl, isobutyl, pentyl, cyclopropyl, cyclobutyl, cyclopentyl, cyclohexyl, trifluormethyl, hydroxy, methoxy, ethoxy, propoxy, isopropoxy, cyclopentyloxy, amino, N-methylamino, N,N-dimethylamino, N-ethylamino, formylamino, acetamido, methoxycarbonylamino, ethoxycarbonylamino, F, Cl, Br, carboxy, methoxycarbonyl, ethoxycarbonyl, aminocarbonyl, methyl-aminocarbonyl, pyrrolidino or piperidino.

$R^3$, $R^{3'}$ independently of each other are particularly preferably H, Hal oder OA, e.g. methoxy or ethoxy.

Accordingly, the invention relates in particular to those compounds of the formula I in which at least one of the radicals mentioned has one of the preferred meanings indicated above. Some preferred groups of compounds can be expressed by the following subformulae Ia to If, which correspond to the formula I and in which the radicals not designated in greater detail have the meanings indicated in the formula I, but in which in Ia $R^1$, $R^2$ in each case idependently of one another are OA, A, OAr or Hal;
in Ib $R^1$, $R^2$ in each case idependently of one another are OA, A, OAr or Hal,
$R^3$ is H, Hal or OA;

in Ic $R^1$, $R^2$ in each case idependently of one another are
OA, A, OAr or Hal,
$R^3$ is H, Hal or OA,
$R^5$ is A;

in Id $R^1$, $R^2$ in each case idependently of one another are
OA, A, OAr or Hal,
$R^3$ is H, Hal or OA,
$R^5$ is A,
A is alkyl with 1 to 6 C-atoms;

in Ie $R^1$, $R^2$ in each case idependently of one another are
OA, A, OAr or Hal,
$R^3$, $R^{3'}$ in each case independently of one another are H, Hal or OA,
$R^5$ is A,
A is alkyl with 1 to 6 C-atoms,
Ar is phenyl;
in If $R^1$, $R^2$ in each case idependently of one another are
OA, A, OAr or Hal,
$R^3$, $R^{3'}$ in each case independently of one another are H, Hal or OA,
$R^5$ is A,
A is alkyl with 1 to 6 C-atoms, which can be substituted by 1 to 5 F and/or Cl atoms,
Ar is phenyl;

and their pharmaceutically usable derivatives, solvates and stereo-isomers, including mixtures thereof in all ratios.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

Preferably, compounds of formula I are synthesized e.g. according to the following reaction scheme:

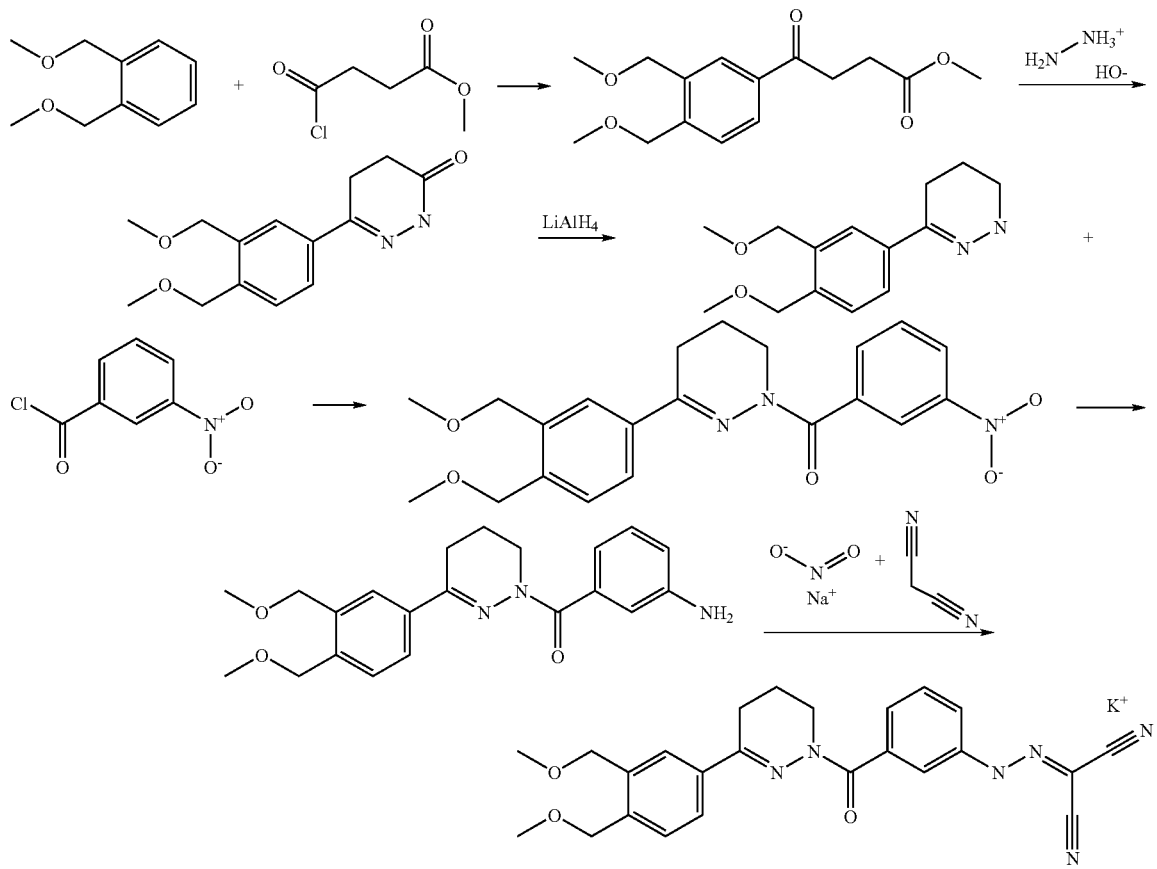

Alternatively, compounds of formula I are synthesized for example according to the following reaction scheme:

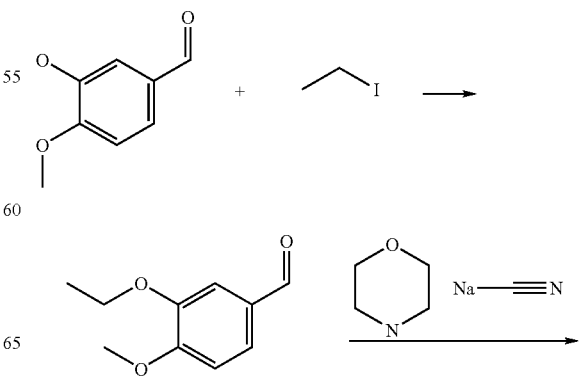

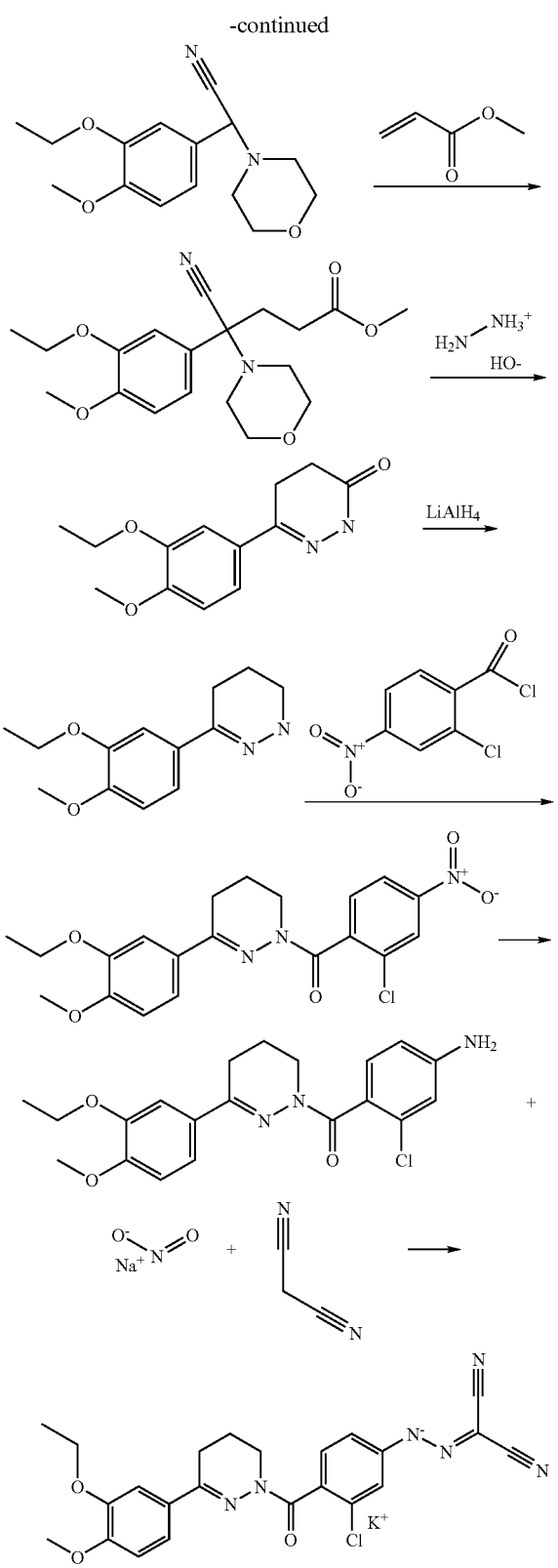

Some of the starting materials of the formula II are known. If they are not known, they can be prepared by methods known per se.

Preferably, compounds of formula II are obtained by reduction of the corresponding nitro compounds according to methods known to the skilled artisan.

Nitro groups are converted for example by hydrogenation on Raney nickel or Pd-carbon in an inert solvent such as methanol or ethanol to amino groups.

Moreover, the invention relates to intermediates of the formula I-I

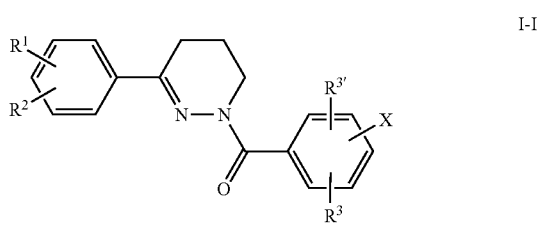

in which $R^1$, $R^2$ in each case independently of one another are H, OH, $OR^5$, —$SR^5$, —$SOR^5$, —$SO_2R^5$ or Hal, $R^1$ and $R^2$ together are also —$OCH_2O$— or —$OCH_2CH_2O$—, $R^3$, $R^{3'}$ in each case independently of one another are $R^5$, OH, $OR^5$, $NH_2$, $NHR^5$, NAA', $NHCOR^5$, $NHCOOR^5$, Hal, COOH, $COOR^5$, $CONH_2$, $CONHR^5$ or $CONR^5A'$, $R^5$ is A or cycloalkyl with 3 to 6 C-atoms, which can be substituted by 1 to 5 F and/or Cl atoms, or —$(CH_2)_n$—Ar, X $NO_2$ or $NH_2$, A, A' in each case independently of one another are alkyl with 1 to 10 C-atoms or are alkenyl with 2 to 8 C-atoms, which can be substituted by 1 to 5 F and/or Cl atoms, A and A' together are also cycloalkyl or cycloalkylene with 3 to 7 C-atoms, wherein one $CH_2$ group can be replaced by O, NH, NA, NCOA or NCOOA, Ar is phenyl, n is 0, 1 or 2, Hal is F, Cl, Br or I and their salts.

Preferred meanings for the substituents are those as mentioned above for the compounds of formula I.

Compounds of formula I—I, wherein X is nitro can preferably be obtained by reacting a compound of formula III

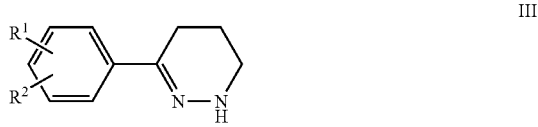

The compounds of the formula I, in which $R^4$ is CN, can preferably be obtained by reacting compounds of the formula II with malodinitrile according to methods known to the skilled artisan.

in which R¹ and R² have the meanings given in claim 1 with a compound of formula IV

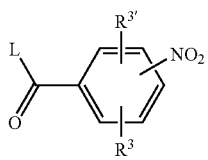

in which

R³ and R³' have the meanings given in claim 1 and

L is Cl, Br, OH or a reactive esterified OH group.

If L is a reactive esterified OH group, it is by preference alkylsulfonyloxy having 1–6 C atoms (preferably methylsulfonyloxy) or arylsulfonyloxy having 6–10 C atoms (preferably phenyl- or p-tolyl-sulfonyloxy, furthermore also 2-naphthalene-sulfonyloxy).

In detail, the reaction of the compounds of the formula II with the compounds of the formula III is carried out in the presence or absence of an inert solvent at temperatures between approximately −20 and approximately 150°, preferably between 20 and 100°.

Examples of suitable inert solvents are hydrocarbons such as hexane, petroleum ether, benzene, toluene or xylene; chlorinated hydrocarbons such as trichloroethylene, 1,2-dichloroethane, carbon tetra-chloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl ether, ethylene glycol monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, or mixtures of the abovementioned solvents.

Pharmaceutical Salts and Other Forms

The above-described compounds of the present invention may be utilized in their final, non-salt form. On the other hand, it is also within the scope of the present invention to utilize those compounds in the form of their pharmaceutically acceptable salts derived from various organic and inorganic acids and bases in accordance with procedures well known in the art. Pharmaceutically acceptable salt forms of the compounds of formula I are prepared for the most part by conventional means. Where the compound of formula I contains a carboxylic acid group, a suitable salt thereof may be formed by reacting the compound with an appropriate base to provide the corresponding base addition salt. Examples of such bases are alkali metal hydroxides including potassium hydroxide, sodium hydroxide, and lithium hydroxide; alkaline earth metal hydroxides such as barium hydroxide and calcium hydroxide; alkali metal alkoxides, e.g., potassium ethanolate and sodium propanolate; and various organic bases such as piperidine, diethanolamine, and N-methylglutamine. Also included are the aluminum salts of the compounds of formula I. For certain compounds of formula I acid addition salts may be formed by treating said compounds with pharmaceutically acceptable organic and inorganic acids, e.g., hydrohalides such as hydrochloride, hydrobromide, hydroiodide; other mineral acids and their corresponding salts such as sulfate, nitrate, phosphate, etc.; and alkyl- and mono-arylsulfonates such as ethanesulfonate, toluenesulfonate, and benzenesulfonate; and other organic acids and their corresponding salts such as acetate, tartrate, maleate, succinate, citrate, benzoate, salicylate, ascorbate, etc.

Accordingly, the pharmaceutically acceptable acid addition salts of the compounds of formula I include, but are not limited to: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, phthalate.

Further, base salts of the compounds of the present invention include, but are not limited to aluminum, ammonium, calcium, copper, ferric, ferrous, lithium, magnesium, manganic, manganous, potassium, sodium, and zinc salts. Preferred among the above recited salts are ammonium; the alkali metal salts sodium and potassium; and the alkaline earth metal salts calcium and magnesium. Salts of the compounds of formula I derived from pharmaceutically acceptable organic non-toxic bases include, but are not limited to salts of primary, secondary, and tertiary amines, substituted amines including naturally occurring substituted amines, cyclic amines, and basic ion exchange resins, e.g., arginine, betaine, caffeine, chloroprocaine, choline, N,N'-dibenzylethylenediamine (benzathine), dicyclohexylamine, diethanol-amine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Compounds of the present invention which comprise basic nitrogen-containing groups may be quaternized with such agents as ($C_1$–$C_4$) alkyl halides, e.g., methyl, ethyl, isopropyl and tert-butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and stearyl chlorides, bromides and iodides; and aryl-($C_1$–$C_4$) alkyl halides, e.g., benzyl chloride and phenethyl bromide. Such salts permit the preparation of both water-soluble and oil soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thlomalate, tosylate, and tromethamine.

The acid addition salts of basic compounds of formula I are prepared by contacting the free base form with a sufficient amount of the desired acid to produce the salt in the conventional manner. The free base may be regenerated by contacting the salt form with a base and isolating the free base in the conventional manner. The free base forms differ from their respective salt forms somewhat in certain physical properties such as solubility in polar solvents, but otherwise the salts are equivalent to their respective free base forms for purposes of the present invention.

As indicated, the pharmaceutically acceptable base addition salts of the compounds of formula I are formed with metals or amines, such as alkali metals and alkaline earth metals, or organic amines. Preferred metals are sodium, potassium, magnesium, and calcium. Preferred organic amines are N,N'-dibenzylethylenediamine, chloroprocaine, choline, diethanolamine, ethylenediamine, N-methyl-D-glucamine, and procaine.

The base addition salts of acidic compounds of the present invention are prepared by contacting the free acid form with a sufficient amount of the desired base to produce the salt in the conventional manner. The free acid form may be regenerated by contacting the salt form with an acid and isolating the free acid form in the conventional manner. The free acid forms differ from their respective salt forms somewhat in physical properties such as solubility in polar solvents, but otherwise the salts are equivalent to their respective free acid forms for purposes of the present invention.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

In light of the above, it can be seen that the expression "pharmaceutically acceptable salt" as used herein is intended to mean an active ingredient comprising a compound of formula I utilized in the form of a salt thereof, especially where said salt form confers on said active ingredient improved pharmacokinetic properties as compared to the free form of said active ingredient or some other salt form of said active ingredient utilized previously. The pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation and excretion of said active ingredient. While the route of administration of the pharmaceutical composition is important, and various anatomical, physiological and pathological factors can critically affect bioavailability, the solubility of said active ingredient is usually dependent upon the character of the particular salt form thereof which it utilized. Further, as the artisan will appreciate, an aqueous solution of said active ingredient will provide the most rapid absorption of said active ingredient into the body of a patient being treated, while lipid solutions and suspensions, as well as solid dosage forms, will result in less rapid absorption of said active ingredient.

Oral ingestion of an active ingredient of formula I is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

A compound of formula I prepared in accordance with the methods described herein can be separated from the reaction mixture in which it is finally produced by any ordinary means known to the chemist skilled in the preparation of organic compounds. Once separated said compound can be purified by known methods. Various methods and techniques can be used as the means for separation and purification, and include, e.g., distillation; recrystallization; column chromatography; ion-exchange chromatography; gel chromatography; affinity chromatography; preparative thin-layer chromatography; and solvent extraction.

Stereoisomers

A compound within the scope of formula I may be such that its constituent atoms are capable of being arranged in space in two or more different ways, despite having identical connectivities. As a consequence, said compound exists in the form of stereoisomers. Systrans isomerism is but one type of stereoisomerism. Where the stereoisomers are non-superimposable mirror images of each other, they are enantiomers which have chirality or handedness, because of the presence of one or more asymmetric carbon atoms in their constituent structure. Enantiomers are optically active and therefore distinguishable because they rotate the plane of polarized light by equal amounts, but in opposite directions.

Where two or more asymmetric carbon atoms are present in a compound of formula I, there are two possible configurations at each said carbon atom. Where two asymmetric carbon atoms are present, for example, there are four possible stereoisomers. Further, these four possible stereoisomers may be arranged into six possible pairs of stereoisomers that are different from each other. In order for a pair of molecules with more than one asymmetric carbon to be enantiomers, they must have different configurations at every asymmetric carbon.

Those pairs that are not related as enantiomers have a different stereochemical relationship referred to as a diastereomeric relationship. Stereoisomers that are not enantiomers are called diastereoisomers, or more commonly, diastereomers.

All of these well known aspects of the stereochemistry of the compounds of formula I are contemplated to be a part of the present invention. Within the scope of the present invention there is thus included compounds of formula I that are stereoisomers, and where these are enantiomers, the individual enantiomers, racemic mixtures of said enantiomers, and artificial, i.e., manufactured mixtures containing proportions of said enantiomers that are different from the proportions of said enantiomers found in a racemic mixture. Where a compound of formula I comprises stereoisomers that are diastereomers, there is included within the scope of said compound the individual diastereomers as well as mixtures of any two or more of said diastereomers in any proportions thereof.

By way of illustration, in the case where there is a single asymmetric carbon atom in a compound of formula I, resulting in the (−)(R) and (+)(S) enantiomers thereof, there is included within the scope of said compound all pharmaceutically acceptable salt forms, prodrugs and metabolites thereof which are therapeutically active and useful in treating or preventing the diseases and conditions described further herein. Where a compound of formula I exists in the form of (−)(R) and (+)(S) enantiomers, there is also included within the scope of said compound the (+)(S) enantiomer alone, or the (−)(R) enantiomer alone, in the case where all, substantially all, or a predominant share of the therapeutic activity resides in only one of said enantiomers, and/or unwanted side effects reside in only one of said enantiomers. In the case where there is substantially no difference between the biological activities of both enantiomers, there is further included within the scope of said compound of formula I the (+)(S) enantiomer and the (−)(R) enantiomer present together as a racemic mixture or as a non-racemic mixture in any ratio of proportionate amounts thereof.

For example, the particular biological activities and/or physical and chemical properties of a pair or set of enantiomers of a compound of formula I where such exist, may suggest use of said enantiomers in certain ratios to constitute a final therapeutic product. By way of illustration, in the case where there is a pair of enantiomers, they may be employed in ratios such as 90% (R)-10% (S); 80% (R)-20% (S); 70% (R)-30% (S); 60% (R)-40% (S); 50% (R)-50% (S); 40% (R)-60% (S); 30% (R)-70% (S); 20% (R)-80% (S); and 10% (R)-90% (S). After evaluating the properties of the various enantiomers of a compound of formula I where such exist, the proportionate amount of one or more of said enantiomers with certain desired properties that will constitute the final therapeutic product can be determined in a straightforward manner.

Isotopes

There is further contemplated to be included within the scope of a compound of formula I isotopically-labelled forms thereof. An isotopically-labelled form of a compound of formula I is identical to said compound but for the fact that one or more atoms of said compound have been replaced by an atom or atoms having an atomic mass or mass number different from the atomic mass or mass number of said atom which is usually found in nature. Examples of isotopes which are readily available commercially and which can be incorporated into a compound of formula I in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. A compound of formula I, a prodrug, thereof, or a pharmaceutically acceptable salt of either which contains one or more of the above-mentioned isotopes and/or other isotopes of other atoms is contemplated to be within the scope of the present invention. An isotopically-labelled compound of formula I may be used in a number of beneficial ways. For example, an isotopically-labelled compound of formula I, e.g., one in which a radioactive isotope such as $^3H$ or $^{14}C$ has been incorporated, will be useful in drug and/or substrate tissue distribution assays. These radioactive isotopes, i.e., tritium, $^3H$, and carbon-14, $^{14}C$, are especially preferred for their ease of preparation and eminent detectability. Incorporation of heavier isotopes, e.g., deuterium, $^2H$, into a compound of formula I will provide therapeutic advantages based on the greater metabolic stability of said isotopically-labelled compound. Greater metabolic stability translates directly into increased in vivo half-life or reduced dosage requirements, which under most circumstances would constitute a preferred embodiment of the present invention. An isotopically-labelled compound of formula I can usually be prepared by carrying out the procedures disclosed in the Synthesis Schemes and related description, Examples, and Preparations herein, substituting a readily available isotopically-labelled reagent for its corresponding non-isotopically-labelled reagent.

Deuterium, $^2H$, can also be incorporated into a compound of formula I for the purpose of manipulating the oxidative metabolism of said compound by way of the primary kinetic isotope effect. The primary kinetic isotope effect is a change of rate for a chemical reaction that results from substitution of isotopic nuclei, which in turn is caused by the change in ground state energies required for covalent bond formation subsequent to said isotopic substitution. Substitution of a heavier isotope will usually result in a lowering of the ground state energy for a chemical bond, thereby causing a reduction in rate for a rate-limiting bond breaking step. If the bond-breaking event occurs on or near a saddle-point region along the coordinate of a multi-product reaction, the product distribution ratios can be altered substantially. By way of illustration, when deuterium is bound to a carbon atom at a nonexchangeable site, rate differences of $k_M/k_D=2-7$ are typical. This difference in rate, aplpied successfully to an oxidatively labile compound of formula I, can dramatically affect the profile of said compound in vivo and result in improved pharmacokinetic properties.

In discovering and developing therapeutic agents, the skilled artisan seeks to optimize pharmacokinetic parameters while retaining desirable in vitro properties. It is a reasonable surmise that many compounds with poor pharmacokinetic profiles suffer from a lability to oxidative metabolism. In vitro liver microsomal assays now available provide valuable information about the course of this oxidative metabolism, which in turn permits the rational design of deuterated compounds of formula I with improved stability through resistance to such oxidative metabolism. Significant improvements in the pharmacokinetic profiles of compounds of formula I are thereby obtained, and can be expressed quantitatively in terms of increases in in vivo half-life (t/2), concentration at maximum therapeutic effect ($C_{max}$), area under the dose response curve (AUC), and F; and in terms of decreases in clearance, dose, and cost-of-goods.

By way of illustration of the above, a compound of formula I which has multiple potential sites for oxidative metabolism, e.g., benzylic hydrogen atoms and hydrogen atoms a to a nitrogen atom, is prepared as a series of analogs in which various combinations of hydrogen atoms are replaced by deuterium atoms so that some, most or all of said hydrogen atoms are replaced with deuterium atoms. Half-life determinations provide an expedient and accurate determination of the extent of improvement in resistance to oxidative metabolism. In this manner it is determined that the half-life of the parent compound can be extended by as much as 100% as the result of such deuterium-for-hydrogen substitution.

Deuterium-for-hydrogen substitution in a compound of formula I can also be used to achieve a favorable alteration in the metabolite profile of the parent compound as a way of diminishing or eliminating unwanted toxic metabolites. For example, where a toxic metabolite arises through an oxidative carbon-hydrogen, C—H, bond scission, the deuterated analog is reasonably expected to greatly diminish or eliminate production of the unwanted metabolite, even in the case where the particular oxidation is not a rate-determining step. Further information concerning the state of the art with respect to deuterium-for-hydrogen substitution may be found, e.g., in Hanzlik et al., J. Org. Chem. 55, 3992–3997, 1990; Reider et al., J. Org. Chem. 52, 3326–3334,1987; Foster, Adv. Drug Res. 14, 1–40, 1985; Gillette et al, Biochemistry 33(10) 2927–2937, 1994; and Jarman et al. Carcinogenesis 16(4), 683–688, 1993.

Therapeutic Applications

Furthermore, the invention relates to the use of compounds of formula I to treat myocardial diseases.

Coronary artery disease is the most common cause of death in the western world. In the presence of a critical stenosed coronary artery, a decrease of blood flow may result in myocardial ischemia. Initiation of reperfusion results, depending on the severity of the preceding ischemic period, in a reversibly or irreversibly injured myocardium, which is characterized by a long-lasting depression or an irreversible loss of contractile function. Depending on the size of the affected myocardial area, an acute or a chronic heart failure may develop.

A particular clinical problem in the above mentioned scenario is the development of restenosis after a primarily successful reperfusion intervention by PTCA, even after stent implantation, thrombolysis or coronary artery bypass grafting.

From experimental animal and clinical studies evidence exists, that in the different above mentioned heart diseases, i.e. coronary artery disease itself, reversible or irreversible myocardial ischemia/reperfusion injury, acute or chronic heart failure and restenosis, including instent-restenosis and stent-in-stent-restenosis, inflammatory processes play a casual role. These inflammatory processes involve resident and invading macrophages as well as neutrophils and $TH_1$ and $TH_2$ helper cells. This leukocyte response produces the characteristic cytokine pattern, involving TNF-α, IL-1β, IL-2, and IL-6, as well as IL-10 and IL-13 (Pulkki KJ: Cytokines and cardiomyocyte death. Ann. Med. 1997 29: 339–343.

Birks EJ, Yacoub MH: The role of nitric oxide and cytokines in heart failure. Coron. Artery. Dis. 1997 8: 389–402).

The formation of these species has been demonstrated in human patients with myocardial ischemia. Animal models show that cytokine production correlates with the invasion of peripheral macrophages and neutrophils which can spread the damage into the still intact myocardium.

The main player in the cytokine response, however, is TNF-a, which integrates inflammatory and pro-apoptotic responses and additionally has a direct negative ionotropic effect on cardiac myocytes (Ceconi C, Curello S, Bachetti T, Corti A, Ferrari R: Tumor necrosis factor in congestive heart failure: a mechanism of disease for the new millennium? Prog. Cardiovasc. Dis. 1998 41: 25–30.

Mann DL: The effect of tumor necrosis factor-alpha on cardiac structure and function: a tale of two cytokines. J. Card. Fail. 1996 2: S165-S172. Squadrito F, Altavilla D, Zingarelli B, et al: Tumor necrosis factor involvement in myocardial ischaemia-reperfusion injury. Eur. J. Pharmacol. 1993 237: 223–230).

It has been shown in animal models of myocardial infarction, that TNF-α is rapidly released during the reperfusion phase (Herskowitz A, Choi S, Ansari M, Wesselingh S: Cytokine mRNA expression in postischemic/reperfused myocardium. Am. J. Pathol. 1995 146: 419–428) and that the protective effects of drugs such as dexamethasone (Arras M, Strasser R, Mohri M, et al: Tumor necrosis factor-alpha is expressed by monocytes/macrophages following cardiac microembolization and is antagonized by cyclosporine.

Basic. Res. Cardiol. 1998 93: 97–107), cyclosporin A (Arras M, Strasser R, Mohri M, et al: Tumor necrosis factor-alpha is expressed by monocytes/macrophages following cardiac microembolization and is antagonized by cyclosporine. Basic. Res. Cardiol. 1998 93: 97–107. Squadrito F, Altavilla D, Squadrito G. et al: Cyclosporin-A reduces leukocyte accumulation and protects against myocardial ischaemia reperfusion injury in rats. Eur. J. Pharmacol. 1999 364: 159–168) or clorichromene (Squadrito F, Altavilla D, Zingarelli B, et al: The effect of cloricromene, a coumarine derivative, on leukocyte accumulation, myocardial necrosis and TNF-alpha production in myocardial ischaemia-reperfusion injury. Life Sci. 1993 53: 341–355) correspond with a reduction of circulating TNF-α.

PDE IV inhibitors of formula I are potent antagonists of macrophage and T-cell cytokine production. They also inhibit the proliferation of T cells.

Consequently, PDE4 inhibition may have a beneficial effect in those myocardial diseases, which are causally linked to cytokine production and inflammatory processes.

As compared with PDE3 inhibitors and the early PDE4 inhibitor Rolipram, preferred PDE4 inhibitors are devoid of hemodynamic side effects, which can be dose limiting for the treatment of most cardiovascular disorders.

The invention was based on the object of discovering new uses of compounds having valuable properties, especially those which may be used to prepare medicaments.

It has been found that the compounds of formula I and their salts combine very valuable pharmacological properties with good tolerability for the treatment of myocardial diseases.

Preferably, the invention provides for the use of the compounds of formula I for preparing a medicament for treating myocardial diseases, where said myocardial diseases show inflammatory and immunological characteristics.

Most preferably, the invention provides for the use of the compounds of formula I for preparing a medicament for treating coronary artery disease, reversible or irreversible myocardial ischemia/reperfusion injury, acute or chronic heart failure and restenosis, including instent-restenosis and stent-in-stent-restenosis.

Preferably, the invention provides for the use of the compounds of formula I for preparing a medicament in treating or preventing one or members selected from the groups of diseases, disorders, and conditions consisting of:
 asthma of whatever type, etiology, or pathogenesis; or
  asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathophysiologic disturbances; extrinsic asthma caused by environmental factors; essential asthma of unknown or inapparent cause; non-atopic asthma; bronchitic asthma; emphysematous asthma; exercise-induced asthma; occupational asthma; infective asthma caused by bacterial, fungal, protozoal, or viral infection; non-allergic asthma; incipient asthma; wheezy infant syndrome;
 chronic or acute bronchoconstriction; chronic bronchitis; small airways obstruction; and emphysema;
 obstructive or inflammatory airways diseases of whatever type, etiology, or pathogenesis; or an obstructive or inflammatory airways disease that is a member selected from the group consisting of asthma; pneumoconiosis; chronic eosinophilic pneumonia; chronic obstructive pulmonary disease (COPD); COPD that includes chronic bronchitis, pulmonary emphysema or dyspnea associated therewith; COPD that is characterized by irreversible, progressive airways obstruction; adult respiratory distress syndrome (ARDS), and exacerbation of airways hyper-reactivity consequent to other drug therapy;

pneumoconiosis of whatever type, etiology, or pathogenesis; or pneumoconiosis that is a member selected from the group consisting of aluminosis or bauxite workers' disease; anthracosis or miners'asthma; asbestosis or steam-fitters' asthma; chalicosis or flint disease; ptilosis caused by inhaling the dust from ostrich feathers; siderosis caused by the inhalation of iron particles; silicosis or grinders' disease; byssinosis or cotton-dust asthma; and talc pneumoconiosis;

bronchitis of whatever type, etiology, or pathogenesis; or bronchitis that is a member selected from the group consisting of acute bronchitis; acute laryngotracheal bronchitis; arachidic bronchitis; catarrhal bronchitis; croupus bronchitis; dry bronchitis; infectious asthmatic bronchitis; productive bronchitis; staphylococcus or streptococcal bronchitis; and vesicular bronchitis;

bronchiectasis of whatever type, etiology, or pathogenesis; or bronchiectasis that is a member selected from the group consisting of cylindric bronchiectasis; sacculated bronchiectasis; fusiform bronchiectasis; capillary bronchiectasis; cystic bronchiectasis; dry bronchiectasis; and follicular bronchiectasis;

seasonal allergic rhinitis; or perennial allergic rhinitis; or sinusitis of whatever type, etiology, or pathogenesis; or sinuisitis that is a member selected from the group consisting of purulent or nonpurulent sinusitis; acute or chronic sinusitis; and ethmoid, frontal, maxillary, or sphenoid sinusitis, rheumatoid arthritis of whatever type, etiology, or pathogenesis; or rheumatoid arthritis that is a member selected from the group consisting of acute arthritis; acute gouty arthritis; chronic inflammatory arthritis; degenerative arthritis; infectious arthritis; Lyme arthritis; proliferative arthritis; psoriatic arthritis; and vertebral arthritis;

gout, and fever and pain associated with inflammation;

an eosinophil-related disorder of whatever type, etiology, or pathogenesis; or an eosinophil-related disorder that is a member selected from the group consisting of eosinophilia; pulmonary infiltration eosinophilia; Loffier's syndrome; chronic eosinophilic pneumonia; tropical pulmonary eosinophilia; bronchopneumonic aspergillosis; aspergilloma; granulomas containing eosinophils; allergic granulomatous angiitis or Churg-Strauss syndrome; polyarteritis nodosa (PAN); and systemic necrotizing vasculitis;

atopic dermatitis; or allergic dermatitis; or allergic or atopic eczema;

urticaria of whatever type, etiology, or pathogenesis; or urticaria that is a member selected from the group consisting of immune-mediated urticaria; complement-mediated urticaria; urticariogenic material-induced urticaria; physical agent-induced urticaria; stressinduced urticaria; idiopathic urticaria; acute urticaria; chronic urticaria; angioedema; cholinergic urticaria; cold urticaria in the autosomal dominant form or in the acquired form; contact urticaria; giant urticaria; and papular urticaria;

conjunctivitis of whatever type, etiology, or pathogenesis; or conjunctivitis that is a member selected from the group consisting of actinic conjunctivitis; acute catarrhal conjunctivitis; acute contagious conjunctivitis; allergic conjunctivitis; atopic conjunctivitis; chronic catarrhal conjunctivitis; purulent conjunctivitis; and vernal conjunctivitis;

uveitis of whatever type, etiology, or pathogenesis; or uveitis that is a member selected from the group consisting of inflammation of all or part of the uvea; anterior uveitis; iritis; cyclitis; iridocyclitis; granulornatous uveitis; nongranulornatous uveitis; phacoantigenic uveitis; posterior uveitis; choroiditis; and chorioretinitis;

psoriasis;

multiple sclerosis of whatever type, etiology, or pathogenesis; or multiple sclerosis that is a member selected from the group consisting of primary progressive multiple sclerosis; and relapsing remitting multiple sclerosis;

autoimmune/inflammatory diseases of whatever type, etiology, or pathogenesis; or an autoimmune/inflammatory disease that is a member selected from the group consisting of autoimmune hematological disorders; hemolytic anemia; aplastic anemia; pure red cell anemia; idiopathic thrombocytopenic purpura; systemic lupus erythematosus; polychondritis; scleroderma; Wegner's granulomatosis; dermatomyositis; chronic active hepatitis; myasthenia gravis; Stevens-Johnson syndrome; idiopathic sprue; autoimmune inflammatory bowel diseases; ulcerative colitis; Crohn's disease; endocrin opthamopathy; Grave's disease; sarcoidosis; alveolitis; chronic hypersensitivity pneumonitis; primary biliary cirrhosis; juvenile diabetes or diabetes mellitus type 1; anterior uveitis; granulornatous or posterior uveitis; keratoconjunctivitis sicca; epidemic keratoconjunctivitis; diffuse interstitial pulmonary fibrosis or interstitial lung fibrosis; idiopathic pulmonary fibrosis; cystic fibrosis; psoriatic arthritis; glomerulonephritis with and without nephrotic syndrome; acute glomerulonephritis; idiopathic nephrotic syndrome; minimal change nephropathy; inflammatory/hyperproliferative skin diseases; psoriasis; atopic dermatitis; contact dermatitis; allergic contact dermatitis; benign familial pemphigus; pemphigus erythematosus; pemphigus foliaceus; and pemphigus vulgaris;

prevention of allogeneic graft rejection following organ transplantation;

inflammatory bowel disease (IBD) of whatever type, etiology, or pathogenesis; or inflammatory bowel disease that is a member selected from the group consisting of ulerative colitis (UC); collagenous colitis; colitis polyposa; transmural colitis; and Crohn's disease (CD);

septic shock of whatever type, etiology, or pathogenesis; or septic shock that is a member selected from the group consisting of renal failure; acute renal failure; cachexia; malarial cachexia; hypophysial cachexia; uremic cachexia; cardiac cachexia; cachexia suprarenalis or Addison's disease; cancerous cachexia; and cachexia as a consequence of infection by the human immunodeficiency virus (HIV);

liver injury;

pulmonary hypertension; and hypoxia-induced pulmonary hypertension;

bone loss diseases; primary osteoporosis; and secondary osteoporosis;

central nervous system disorders of whatever type, etiology, or pathogenesis; or a central nervous system disorder that is a member selected from the group consisting of depression; Parkinson's disease; learning and memory impairment; tardive dyskinesia; drug. dependence; arteriosclerotic dementia; and dementias that accompany Huntington's chorea, Wilson's disease, paralysis agitans, and thalamic atrophies;

infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3; cytornegalovirus, CMV; influenza; adenoviruses; and Herpes viruses, including Herpes zoster and Herpes simplex;

yeast and fungus infections wherein said yeast and fungi are sensitive to upregulation by TNF-α or elicit TNF-α production in their host, e.g., fungal meningitis; particularly when administered in conjunction with other drugs of choice for the treatment of systemic yeast and fungus infections, including but are not limited to, polymixins, e.g., Polymycin B; imidazoles, e.g., clotrimazole, econazole, miconazole, and ketoconazole; triazoles, e.g., fluconazole and itranazole; and amphotericins, e.g., Amphotericin B and liposomal Amphotericin B;

ischemia-reperfusion injury; autoimmune diabetes; retinal autoimmunity; chronic lymphocytic leukemia; HIV infections; lupus erythematosus; kidney and ureter disease; urogenital and gastrointestinal disorders; and prostate diseases.

In particular, compounds of formula I are useful in the treatment of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: asthma, acute respiratory distress syndrome, chronic pulmonary inflammatory disease, bronchitis, chronic obstructive airway disease, and silicosis; (3) infectious diseases and conditions comprising: sepsis, septic shock, endotoxic shock, gram negative, sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, psoriasis, and allergic rhinitis; and (5) other diseases and conditions comprising: bone resorption diseases; reperfusion injury; cachexia secondary to infection or malignancy; cachexia secondary to human acquired immune deficiency syndrome (AIDS), human immunodeficiency virus (HIV) infection, or AIDS related complex (ARC); keloid formation; scar tissue formation; type 1 diabetes mellitus; and leukemia.

The present invention further relates to the combination of a compound of Formula I together with one or more members selected from the group consisting of the following:

(a) leukotriene biosynthesis inhibitors: 5-lipoxygenase (5-LO) inhibitors and 5-lipoxygenase activating protein (FLAP) antagonists selected from the group consisting of zileuton; ABT-761; fenleuton; tepoxalin; Abbott-79175; Abbott-85761; N-(5-substituted) thiophene-2-alkylsulfonamides; 2,6-di-tert-butylphenol hydrazones;the class of methoxytetrahydropyrans which includes Zeneca ZD-2138; the compound SB-210661 and the class to which it belongs; the class of pyridinyl-substituted 2-cyano-naphthafene compounds to which L 739,010 belongs; the class of 2-cyanoquinoline compounds to which L-746,530 belongs; the classes of indole and quinoline compounds to which MK-591, MK-886, and BAY×1005 belong; (b) receptor antagonists for leukotrienes LTB4, LTC4, LTD4, and LTE4 selected from the group consisting of the phenothiazin-3-one class of compounds to which L-651,392 belongs; the class of amidino compounds to which CGS-25019c belongs; the class of benzoxaolamines to which ontazolast belongs; the class of benzene-carboximidamides to which BIIL 284/260 belongs; and the classes of ompounds to which zafirlukast, ablukast, montelukast, pranlukast, verlukast (MK-679), RG-12525, Ro-245913, iralukast (CGP 45715A), and BAY×7195 belong; (c) PDE4 inhibitors; (d) 5-Lipoxygenase (5-1-0) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of LTB4, LTC4, LTD4, and LTE4; (g) antihistaminic H, receptor antagonists including cetirizine, loratadine, desioratadine, fexofenadine, astemizole, azelastine, and chlorpheniramine; (h) gastroprotective H2 receptor antagonists; (i) $\alpha_1$- and $\alpha_2$-adrenoceptor agonist vasoconstrictor sympathomimetic agents administered orally or topically for decongestant use, including propyl hexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; j) $\alpha_1$- and $\alpha_2$-adrenoceptor agonists in combination with inhibitors of 5-lipoxygenase (5-LO); (k) anticholinergic agents including ipratropium bromide; tiotropiurn bromide; oxitropium bromide; pirenzepine; and telenzepine; (l) $\beta_1$- to $\beta_4$ adrenoceptor agonists including etaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate; (o) muscarinic receptor (MI, M2, and M3) antagonists; (p) COX-1 inhibitors (NSAIDs); COX-2 selective inhibitors including rofecoxib; and nitric oxide NSAIDs; (q) insulin-like growth factor type I (IGF-1) mimetics; (r) ciclesonide; (s) inhaled glucocorticoids with reduced systemic side effects, including prednisone, prednisolone, flunisolide, triamcinolone acetonide, beclomethasone dipropionate, budesonide, fluticasone propionate, and mometasone furoate; (t) tryptase inhibitors; (u) platelet activating factor (PAF) antagonists; (v) monoclonal antibodies active against endogenous inflammatory entities; (w) IPL 576; (x) antitumor necrosis factor (TNFα) agents including Etanercept, Infliximab, and D2E7; (y) DMARDs including Leflunomide; (z) TCR peptides; (aa) interleukin converting enzyme (ICE) inhibitors; (bb) IMPDH inhibitors; (cc) adhesion molecule inhibitors including VLA-4 antagonists; (dd) cathepsins; (ee) MAP kinase inhibitors; (ff) glucose-6 phosphate dehydrogenase inhibitors; (gg) kinin-131- and B2-receptor antagonists; (hh) gold in the form of an aurothio group together with various hydrophilic groups; (ii) immunosuppressive agents, e.g., cyclosporine, azathioprine, and methotrexate; (jj) anti-gout agents, e.g., colchicine; (kk) xanthine oxidase inhibitors, e.g., allopurinol; (ll) uricosuric agents, e.g., probenecid, sulfinpyrazone, and benzbromarone; (mm) antineoplastic agents, especially antimitotic drugs including the vinca alkaloids such as vinblastine and vincristine; (nn) growth hormone secretagogues; (oo) inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11); (pp)-transforming growth factor (TGFβ); (qq) platelet-derived growth factor (PDGF); (rr) fibroblast growth factor, e.g., basic fibroblast growth factor (bFGF); (ss) granulocyte macrophage colony stimulating factor (GM-CSF); (tt) capsaicin; (uu) Tachykinin $NK_1$ and $NK_3$ receptor antagonists selected from the group consisting of NKP-608C; SB233412 (talnetant); and D-4418; and (vv) elastase inhibitors selected from the group consisting of UT-77 and ZD-0892.

The present invention relates to a combination of a compound of formula I together with one or more additional therapeutic agents to be co-administered to a patient to obtain some particularly desired therapeutic end result. The second, etc. therapeutic agent may also be one or more compounds as described above or one or more PDE4 inhibitors known in the art and described in detail herein. More typically, the second, etc. therapeutic agent will be selected from a different class of therapeutic agents. These selections are described in detail below.

As used herein, the terms co-administration", "co-administered", and "in combination with", referring to the compounds of formula I and one or more other therapeutic agents, is intended to mean, and does refer to and include the following:

(a) simultaneous administration of such combination of compound(s) and therapeutic agent(s) to a patient in need of treatment, when such components are formulated together into a single dosage form which releases said components at substantially the same time to said patient;

(b) substantially simultaneous administration of such combination of compound(s) and therapeutic agent(s) to a patient in need of treatment, when such components are formulated apart from each other into separate dosage forms which are ingested at substantially the same time by said patient, whereupon said components are released at substantially the same time to said patient;

(c) sequential administration of such combination of compound(s) and therapeutic agent(s) to a patient in need of treatment, when such components are formulated apart from each other into separate dosage forms which are ingested at consecutive times by said patient with a significant time interval between each ingestion, whereupon said components are released at substantially different times to said patient;

and (d) sequential administration of such combination of compound(s) and therapeutic agent(s) to a patient in need of treatment, when such components are formulated together into a single dosage form which releases said components in a controlled manner whereupon they are concurrently, consecutively, and/or overlappingly ingested at the same and/or different times by said patient.

Combinations with Leukotriene Biosynthesis Inhibitors: 5-Lipoxygenase (5-LO) Inhibitors and 5-Lipoxygenase Activating Protein (FLAP) Antagonists One or more of the compounds of formula I is used in combination with leukotriene biosynthesis inhibitors, i.e., 5-lipoxygenase inhibitors and/or 5-lipoxygenase activating protein antagonists, to form embodiments of the present invention. 5-Lipoxygenase (5-LO) is one of two groups of enzymes that metabolize arachidonic acid, the other group being the cyclooxygenases, COX-1 and COX-2.

The 5-lipoxygenase activating protein is an 18 kDa membrane-bound, arachidonate-binding protein which stimulates the conversion of cellular arachidonic acid by 5-lipoxygenase. The arachidonic acid is converted into 5-hydroperoxyeicosatetraenoic acid (5-HPETE), and this pathway eventually leads to the production of inflammatory leukotrienes; consequently, blocking the 5-lipoxygenase activating protein or the 5-lipoxygenase enzyme itself provides a desirable target for beneficially interfering with that pathway. One such 5-lipoxygenase inhibitor is zileuton.

Among the classes of leukotriene synthesis inhibitors which are useful for forming therapeutic combinations with the compounds of formula I are the following:

(a) redox-active agents which include N-hydroxyureas; N-alkyl-hydroxamid acids; selenite; hydroxybenzofurans; hydroxylamines; and catechols; see Ford-Hutchinson et al., "5-Lipoxygenase," Ann. Rev. Biochem. 63, 383–417, 1994; Weitzel and Wendel, "Selenoenzymes regulate the activity of leukocyte 5-lipoxygenase via the peroxide tone," J. Biol. Chem. 268, 6288–92, 1993; Björnstedt et al. "Selenite incubated with NADPH and mammalian thioredoxin reductase yields selenide, which inhibits lipoxygenase and changes the electron spin resonance spectrum of the active site iron," Biochemistry 35, 8511–6, 1996; and Stewart et al., "Structure-activity relationships of N-hydroxyurea 5-lipoxygenase inhibitors," J. Med. Chem. 40, 1955–68, 1997;

(b) alkylating agents and compounds which react with SH groups have been found to inhibit leukotriene synthesis in vitro; see Larsson et al., "Effects of 1-chloro-2,4,6-trinitrobenzene on 5-lipoxygenase activity and cellular leukotriene synthesis," Biochem. Pharmacol. 55, 863–71, 1998; and (c) competitive inhibitors of 5-lipoxygenase, based on thiopyranoindole and methoxyalkyl thiazole structures which may act as non-redox inhibitors of 5-lipoxygenase; see Ford-Hutchinson et al., Ibid.; and Hamel et al., "Substituted (pyridylmethoxy)naphthalenes as potent and orally active 5-lipoxygenase inhibitors—synthesis, biological profile, and pharmacokinetics of L-739,01 0," J. Med. Chem. 40, 2866–75, 1997.

The observation that arachidonoyl hydroxyamate inhibits 5-lipoxygenase has led to the discovery of clinically useful selective 5-lipoxygenase inhibitors such as the N-hydroxyurea derivatives zileuton and ABT-761, represented below:

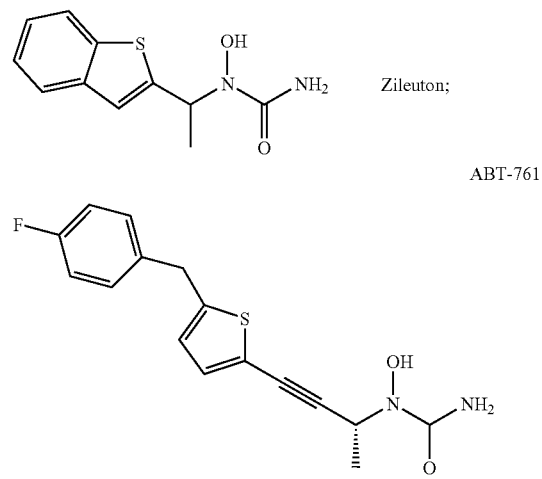

Another N-hydroxyurea compound is fenleuton (Abbott-76745):

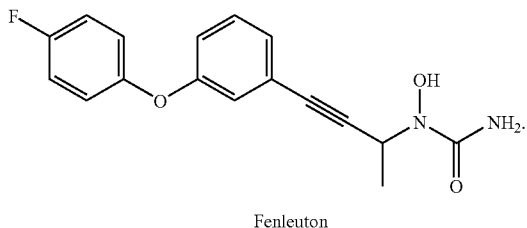

Fenleuton

Another N-hydroxyurea compound is Abbott-79175

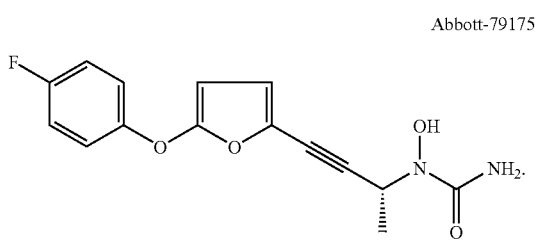

Abbott-79175

Abbott-79175 has a longer duration of action than zileuton; Brooks et al, J. Pharm. Exp. Therapeut 272 724, 1995.

A still further N-hydroxyurea compound is Abbott-85761

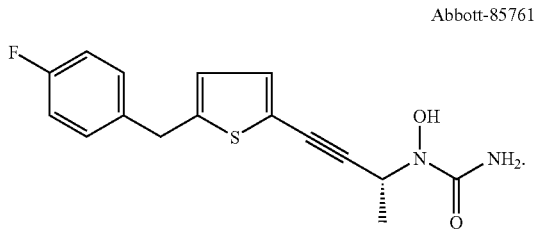

Abbott-85761

Abbott-85761 is delivered to the lung by aerosol administration of a homogeneous, physically stable and nearly monodispersed formulation; Gupta et al., "Pulmonary delivery of the 5-lipoxygenase inhibitor, Abbott-85761, in beagle dogs," International Journal of Pharmaceutics 147, 207–218, 1997.

Fenleuton, Abbott-79175, Abbott-85761 or any of the above-described derivatives thereof or of tepoxalin, are combined with the compounds of formula I to form embodiments of the present invention.

Since the elucidation of the 5-LO biosynthetic pathway, there has been an ongoing debate as to whether it is more advantageous to inhibit the 5-lipoxygenase enzyme or to antagonize peptido- or non-peptido leukotriene receptors. Inhibitors of 5-lipoxygenase are deemed to be superior to LT-receptor antagonists, since 5-lipoxygenase inhibitors block the action of the full spectrum of 5-LO products, whereas LT-antagonists produce narrower effects. Nevertheless, embodiments of the present invention include combinations of the compounds of formula I with LT-antagonists as well as 5-LO inhibitors, as described below. Inhibitors of 5-lipoxygenase having chemical structures that differ from the classes of N-hydroxyureas and hydroxamic acids described above are also used in combination with the compounds of formula I to form further embodiments of the present invention. An example of such a different class is the N-(5-substituted)-thiophene-2-alkylsulfonamides of following formula

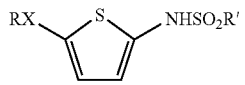

where X is O or S; R' is methyl, iso-propyl, n-butyl, n-octyl, or phenyl; and R is n-pentyl, cyclohexyl, phenyl, tetrahydro-1-naphthyl, 1- or 2-naphthyl, or phenyl mono- or di-substituted by Cl, F, Br, $CH_3$, $OCH_3$, $SCH_3$, $SO_2CH_3$, $CF_3$, or iso-propyl. A preferred compound is

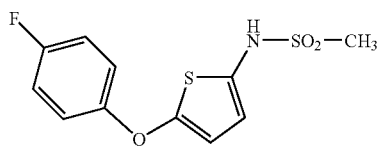

A further description of these compounds may be found in Beers et al., "N-(5-substituted) thiophene-2-alkylsulfonamides as potent inhibitors of 5-lipoxygenase," Bioorganic & Medicinal Chemistry 5(4), 779–786, 1997.

Another distinct class of 5-lipoxygenase inhibitors is that of the 2,6-di-tert-butylphenol hydrazones described in Cuadro et al., "Synthesis and biological evaluation of 2,6-di-tert.-butylphenol hydrazones as 5-lipoxygenase inhibitors," Bioorganic & Medicinal Chemistry 6, 173–180, 1998. Compounds of this type are represented by

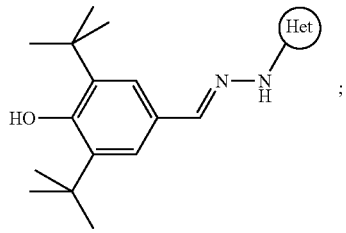

where "Het" is benzoxazol-2-yl; benzothiazol-2-yl; pyridin-2-yl; pyrazin-2-yl; pyrimidin-2-yl; 4-phenylpyrimidin-2-yl; 4,6-diphenylpyrimidin-2-yl; 4-methylpyrimidin-2-yl; 4,6-dimethylpyrimidin-2-yl; 4-butylpyrimidin-2-yl; 4,6-dibutylpyrimidin-2-yl; and 4-methyl-6-phenylpyrimidin-2-yl.

The N-(5-substituted)-thiophene-2-alkylsulfonamides or the 2,6-di-tert-butylphenol hydrazones or any of the above-described derivatives thereof, are combined with the compounds of formula I mentioned above to form embodiments of the present invention.

A further distinct class of 5-lipoxygenase inhibitors is that of methoxytetrahydropyrans to which Zeneca ZD-2138 belongs

ZD-1238

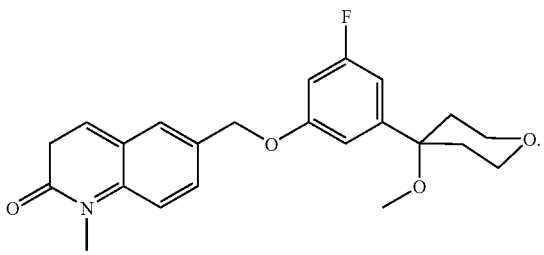

ZD-2138 is highly selective and highly active orally in a number of species and has been evaluated in the treatment of asthma and rheumatoid arthritis by oral admininstration. Further details concerning ZD-2138 and derivatives thereof are disclosed in Crawley et al., J. Med. Chem., 35, 2600, 1992; and Crawley et al., J. Med. Chem. 36, 295, 1993.

Another distinct class of 5-lipoxygenase inhibitors is that to which the SmithKline Beecham compound SB-210661 belongs

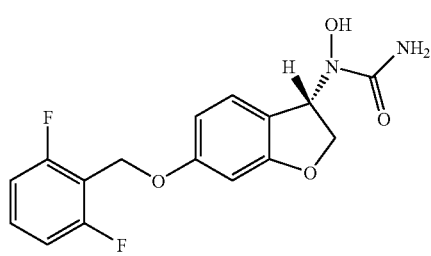

Two further distinct and related classes of 5-lipoxygenase inhibitors comprise a series of pyridinyl-substituted 2-cyanonaphthalene compounds and a series of 2-cyanoquinoline compounds discovered by Merck Frosst. These two classes of 5-lipoxygenase inhibitors are exemplified by L-739,01 0 and L-746,530, respectively:

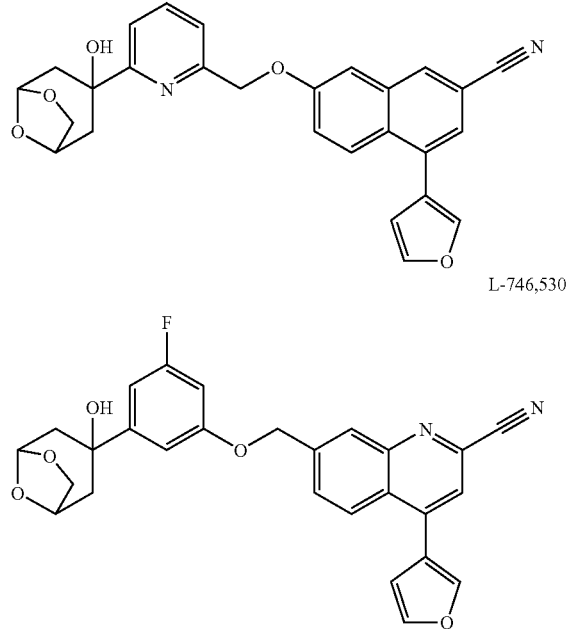

L-739,010

L-746,530

Details concerning L-739,010 and L-746,530 are disclosed in Dubé et al., "Quinolines as potent 5-lipoxygenase inhibitors: synthesis and biological profile of L-746,530," Bioorganic & Medicinal Chemistry 8, 1255–1260, 1998; and in WO 95/03309 (Friesen et al.).

The class of methoxytetrahydropyrans including Zeneca ZD-2138; or the lead compound SB-210661 and the class to which it belongs; or the series of pyridinyl-substituted 2-cyanonaphthalene compounds to which L 739,010 belongs, or the series of 2-cyanoquinoline compounds to which L-746,530 belongs; or any of the above-described derivatives of any of the above-mentioned classes, are combined with the compounds of formula I to form embodiments of the present invention.

In addition to the 5-lipoxygenase enzyme, the other endogenous agent which plays a significant role in the biosynthesis of the leukotrienes is the 5-lipoxygenase activating protein (FLAP). This role is an indirect one, in contrast to the direct role of the 5-lipoxygenase enzyme.

Nevertheless, antagonists of the 5-lipoxygenase activating protein are employed to inhibit the cellular synthesis of leukotrienes, and as such are also used in combination with the compounds of formula I to form embodiments of the present invention.

Compounds which bind to the 5-lipoxygenase activating protein and thereby block utilization of the endogenous pool of archidonic acid which is present have been synthesized from indole and quinoline structures; see Ford-Hutchinson et al., Ibid.; Rouzer et al. "WK-886, a potent and specific leukotriene biosynthesis inhibitor blocks and reverses the membrane association of 5-lipoxygenase in ionophore-challenged leukocytes," J. Biol. Chem. 265, 1436–42, 1990; and Gorenne et al., "{(R)-2-quinolin-2-yl-methoxy)phenyl)-2-cyclopentyl acetic acid} (BAY×1005), a potent leukotriene synthesis inhibitor: effects on anti-IgE challenge in human airways," J. Pharmacol. Exp. Ther. 268, 868–72, 1994.

MK-591, which has been designated quiflipon sodium, is represented below

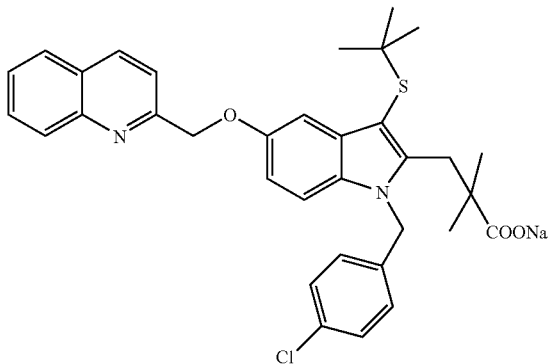

MK-591

The above-mentioned indole and quinoline classes of compounds and the specific compounds MK-591, IVIK-886, and BAY×1005 to which they belong, or any of the above-described derivatives of any of the above-mentioned classes, are combined with the compounds of formula I to form embodiments of the present invention.

Combinations with Receptor Antagonists for Leukotrienes $LTB_4$, $LTC_4$ $LTD_4$, and $LTE_4$ One or more compounds of formula I is used in combination with receptor antagonists for leukotrienes $LTB_4$, $LTC_4$, $LTD_4$, and $LTE_4$. The most significant of these leukotrienes in terms of mediating inflammatory response, are $LTB_4$ and $LTD_4$. Classes of antagonists for the receptors of these leukotrienes are described in the paragraphs which follow.

4-Bromo-2,7-diemethoxy-3H-phenothiazin-3-ones, including L-651,392, are potent receptor antagonists for LTB₄ that are described in U.S. Pat. No. 4,939,145 (Guindon et al.) and U.S. Pat. No. 4,845,083 (Lau et al.)

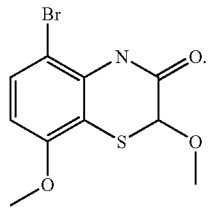

L-651,392

A class of amidino compounds that includes CGS-25019c is described in U.S. Pat. No. 5,451,700 (Morrissey and Suh); U.S. Pat. No. 5,488,160 (Morrissey); and U.S. Pat. No. 5,639,768 (Morrissey and Suh). These receptor antagonists for LTB₄ are typified by CGS-25019c, which is represented below:

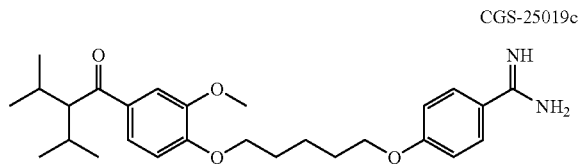

CGS-25019c

Ontazolast, a member of a class of benzoxaolamines that are receptor antagonists for LTB₄, is described in EP 535 521 (Anderskewitz et A):

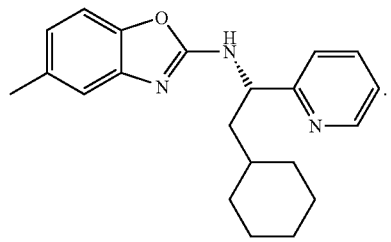

Ontozolast

The same group of workers has also discovered a class of benzenecarboximidamides which are receptor antagonists for LTB₄, described in WO 97/21670 (Anderskewitz et al.); and WO 98/11119 (Anderskewitz et l.); and which are typified by BIIL 284/260:

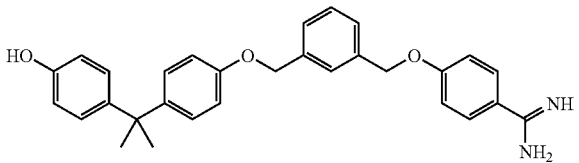

BIIL 284/260

Zafirlukast is a receptor antagonist for LTC₄, LTD₄, and LTE4 which is sold commercially under the name Accolate®. It belongs to a class of heterocyclic amide derivatives described in U.S. Pat. No. 4,859,692 (Bernstein et al.); U.S. Pat. No. 5,319,097 (Holohan and Edwards); U.S. Pat. No. 5,294,636 (Edwards and Sherwood); U.S. Pat. No. 5,482,963; U.S. Pat. No. 5,583,152 (Bernstein et al.); and U.S. Pat. No. 5,612,367 (Timko et al.):

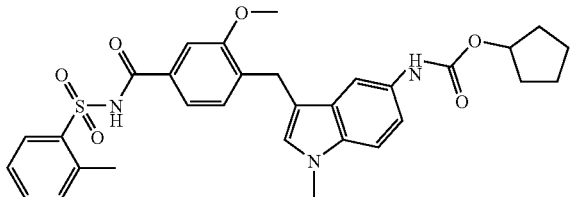

Zafirlukast

Ablukast is a receptor antagonist for LTD₄ that is designated Ro 23-3544/001:

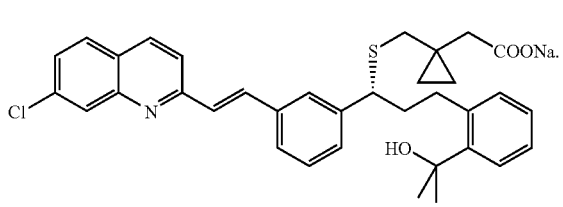

Ablukast

Montelukast is a receptor antagonist for LTD₄ which is sold commercially under the name Singulair® and is described in U.S. Pat. No. 5,565,473:

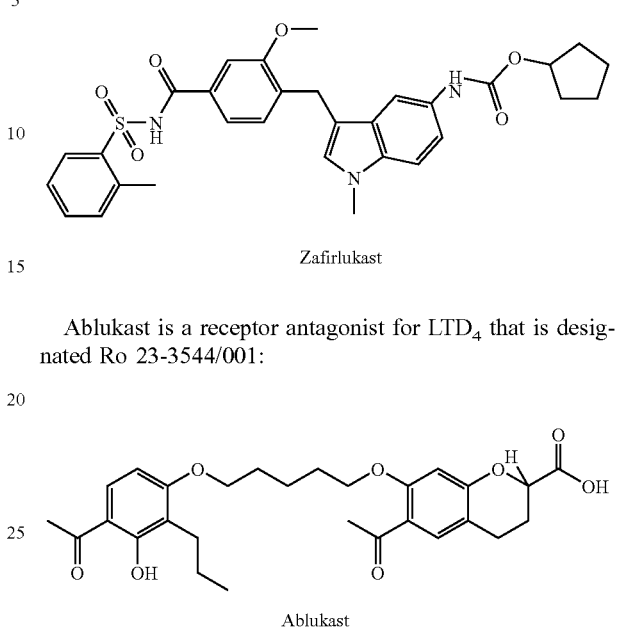

Montekulast

Other receptor antagonists for LTD₄ include praniukast, verlukast (MK-679), RG-12525, Ro-245913, iralukast (CGP 45715A), and BAYx7195.

The above-mentioned phenothiazin-3-one class of compounds, including L-651,392; the class of amidino compounds that includes CGS-25019c; the class of benzoxaolamines which includes Ontazolast; the class of benzenecarboximidamides which is typified by BIIL 284/260; the heterocyclic amide derivatives including Zafirlukast; Ablukast and Montelukast and the classes of compounds to which they belong; or any of the above-described derivatives of any of the above-mentioned classes, are combined with the compounds of formula I to form embodiments of the present invention.

Combinations with Other Therapeutic Agents

One or more compounds of formula I are used together with other therapeutic agents as well as non-therapeutic agents to form combinations that are further embodiments of the present invention and that are useful in the treatment of a significant number of different diseases, disorders, and conditions described herein. Said embodiments comprise one or more compounds of formula I together with one or more of the following:

(a) PDE4 inhibitors;
(b) 5-Lipoxygenase (5-LO) inhibitors; or 5-lipoxygenase activating protein (FLAP) antagonists;
(c) Dual inhibitors of 5-lipoxygenase (5-LO) and antagonists of platelet activating factor (PAF);
(d) Leukotriene antagonists (LTRAs) including antagonists of $LTB_4$, $LTC_4$, $LTD_4$, and $LTE_4$;
(e) Antihistaminic $H_1$ receptor antagonists including cetirizine, loratadine, desloratadine, fexofenadine, astemizole, azelastine, and chlorpheniramine;
(f) Gastroprotective $H_2$ receptor antagonists;
(g) $\alpha_1$- and $\alpha_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride;
(h) $\alpha_1$- and $\alpha_2$-adrenoceptor agonists in combination with inhibitors of 5-lipoxygenase (5-LO);
(i) Anticholinergic agents including ipratropium bromide; tiotropium bromide; oxitropium bromide; pirenzepine; and telenzepine;
(j) $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol;
(k) Theophylline and aminophylline;
(l) Sodium cromoglycate;
(m) Muscarinic receptor (M1, M2, and M3) antagonists;
(n) COX-1 inhibitors (NSAIDs); COX-2 selective inhibitors including rofecoxib; and nitric oxide NSAIDs;
(o) Insulin-like growth factor type I (IGF-1) mimetics;
(p) Ciclesonide;
(q) Inhaled glucocorticoids with reduced systemic side effects, including prednisone, prednisolone, flunisolide, triamcinolone acetonide, beclomethasone dipropionate, budesonide, fluticasone propionate, and mometasone furoate;
(r) Tryptase inhibitors;
(s) Platelet activating factor (PAF) antagonists;
(t) Monoclonal antibodies active against endogenous inflammatory entities;
(u) IPL 576;
(v) Anti-tumor necrosis factor (TNFα) agents including Etanercept, Infliximab, and D2E7;
(w) DMARDs including Leflunomide;
(x) TCR peptides;
(y) Interleukin converting enzyme (ICE) inhibitors;
(z) IMPDH inhibitors;
(aa) Adhesion molecule inhibitors including VLA-4 antagonists;
(bb) Cathepsins;
(cc) MAP kinase inhibitors;
(dd) Glucose-6 phosphate dehydrogenase inhibitors;
(ee) Kinin-$B_1$ and $B_2$-receptor antagonists;
(ff) Gold in the form of an aurothio group together with various hydrophilic groups;
(gg) Immunosuppressive agents, e.g., cyclosporine, azathioprine, and methotrexate;
(hh) Anti-gout agents, e.g., colchicine;
(ii) Xanthine oxidase inhibitors, e.g., allopurinol;
(jj) Uricosuric agents, e.g., probenecid, sulfinpyrazone, and benzbromarone;
(kk) Antineoplastic agents, especially antimitotic drugs including the vinca alkaloids such as vinblastine and vincristine;
(ll) Growth hormone secretagogues;
(mm) Inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11);
(nn) Transforming growth factor (TGFβ);
(oo) Platelet-derived growth factor (PDGF);
(pp) Fibroblast growth factor, e.g., basic fibroblast growth factor (bFGF);
(qq) Granulocyte macrophage colony stimulating factor (GM-CSF);
(rr) Capsaicin;
(ss) Tachykinin $NK_1$ and $NK_3$ receptor antagonists selected from the group consisting of NKP-608C; SB-233412 (talnetant); and D-4418;
(tt) Elastase inhibitors selected from the group consisting of UT-77 and ZD-0892; and
(uu) Adenosine A2a receptor agonists.

Pharmaceutical Compositions and Formulations

The description which follows concerns the manner in which the compounds of formula I, together with other therapeutic agents or non-therapeutic agents where these are desired, are combined with what are for the most part conventional pharmaceutically acceptable carriers to form dosage forms suitable for the different routes of administration which are utilized for any given patient, as well as appropriate to the disease, disorder, or condition for which any given patient is being treated.

The pharmaceutical compositions of the present invention comprise any one or more of the above-described inhibitory compounds of the present invention, or a pharmaceutically acceptable salt thereof as also above-described, together with a pharmaceutically acceptable carrier in accordance with the properties and expected performance of such carriers which are well-known in the pertinent art.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The compounds of formula I may be utilized in the form of acids, esters, or other chemical classes of compounds to which the compounds described belong. It is also within the scope of the present invention to utilize those compounds in the form of pharmaceutically acceptable salts derived from various organic and inorganic acids and bases. An active ingredient comprising a preferred compound is often Utilized in the form of a salt thereof, especially where said salt form confers on said active ingredient improved pharmacokinetic properties as compared to the free form of said active ingredient or some other salt form of said active ingredient utilized previously. The pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation and excretion of said active ingredient. While the route of administration of the pharmaceutical composition is important, and various anatomical, physiological and pathological factors can critically affect bioavailability, the solubility of said active ingredient is usually dependent upon the character of the particular salt form thereof which it utilized. Further, as the artisan understands, an aqueous solution of said active ingredient will provide the most rapid absorption of said active ingredient into the body of a patient being treated, while lipid solutions and suspensions, as well as solid dosage forms, will result in less rapid absorption of said active ingredient. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different harmaceutically acceptable salt forms may be effective in overcoming or alleviating one or more of the above-recited problems encountered with absorption of oral dosage forms.

Among the pharmaceutical salts recited further above, those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of formula I contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described inhibitory compounds, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipients, adjuvants, vehicles, solubilization aids, viscosity modifiers, preservatives and other agents well known to the artisan for providing favorable properties in the final pharmaceutical composition. In order to illustrate such carriers, there follows a brief survey of pharmaceutically acceptable carriers that may be used in the pharmaceutical compositions of the present invention, and thereafter a more detailed description of the various types of ingredients. Typical carriers include but are by no means limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; hydrogenated palm oils; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the carriers used in the pharmaceutical compositions of the present invention comprise various classes and species of additives which are members independently selected from the groups consisting essentially of those recited in the following paragraphs.

Acidifying and alkalizing agents are added to obtain a desired or predetermined pH and comprise acidifying agents, e.g., acetic acid, glacial acetic acid, malic acid, and propionic acid. Stronger acids such as hydrochloric acid, nitric acid and sulfuric acid may be used but are less preferred. Alkalizing agents include, e.g., edetol, potassium carbonate, potassium hydroxide, sodium borate, sodium carbonate, and sodium hydroxide. Alkalizing agents which contain active amine groups, such as diethanolamine and trolamine, may also be used.

Aerosol propellants are required where the pharmaceutical composition is to be delivered as an aerosol under significant pressure. Such propellants include, e.g., acceptable fluorochlorohydrocarbons such as dichlorodifluoromethane, dichlorotetrafluoroethane, and trichloro-monofluoromethane; nitrogen; or a volatile hydrocarbon such as butane, propane, isobutane or mixtures thereof.

Antimicrobial agents including antibacterial, antifungal and antiprotozoal agents are added where the pharmaceutical composition is topically applied to areas of the skin which are likely to have suffered adverse conditions or sustained abrasions or cuts which expose the skin to infection by bacteria, fungi or protozoa. Antimicrobial agents include such compounds as benzyl alcohol, chlorobutanol, phenylethyl alcohol, phenylmercuric acetate, potassium sorbate, and sorbic acid. Antifungal agents include such compounds as benzoic acid, butylparaben, ethylparaben, methylparaben, propylparaben, and sodium benzoate.

Antimicrobial preservatives are added to the pharmaceutical compositions of the present invention in order to protect them against the growth of potentially harmful microorganisms, which usually invade the aqueous phase, but in some cases can also grow in the oil phase of a composition. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, and trisodium ethylenediamine tetracetate (EDTA).

Preservatives, are preferably employed in amounts ranging from about 0.01% to about 2.0% by weight of the total composition.

Antioxidants are added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols.

Buffering agents are used to maintain a desired pH of a composition once established, from the effects of outside agents and shifting equilibria of components of the composition. The buffering may be selected from among those familiar to the artisan skilled in the preparation of pharmaceutical compositions, e.g., calcium, acetate, potassium metaphosphate, potassium phosphate monobasic, and tartaric acid.

Chelating agents are used to help maintain the ionic strength of the pharmaceutical composition and bind to and effectively remove destructive compounds and metals, and include, e.g., edetate dipotassium, edetate disodium, and edetic acid.

Dermatologically active agents are added to the pharmaceutical compositions of the present invention where they are to be applied topically, and include, e.g., wound healing agents such as peptide derivatives, yeast, panthenol, hexylresorcinol, phenol, tetracycline hydrochloride, lamin and kinetin; retinoids for treating skin cancer, e.g., retinol, tretinoin, isotretinoin, etretinate, acitretin, and arotinoid; mild antibacterial agents for treating skin infections, e.g., resorcinol, salicylic acid, benzoyl peroxide, erythromycin-benzoyl peroxide, erythromycin, and clindamycin; antifungal agents for treating tinea corporis, tinea pedis, candidiasis and tinea versicolor, e.g., griseofulvin, azoles such as miconazole, econazole, itraconazole, fluconazole, and ketoconazole, and allylamines such as naftifine and terfinafine; antiviral agents for treating cutaneous herpes simplex, herpes zoster, and chickenpox, e.g., acyclovir, famciclovir, and valacyclovir; antihistamines for treating pruritis, atopic and contact dermatitis, e.g., diphenhydramine, terfenadine, asternizole, loratadine, cetirizi, ne, acrivastine, and temelastine; topical anesthetics for relieving pain, irritation and itching, e.g., benzocaine, lidocaine, dibucaine, and pramoxine hydrochloride; topical analgesics for relieving pain and inflammation, e.g., methyl salicylate, camphor, menthol, and resorcinol; topical antiseptics for preventing infection, e.g., benzalkonium chloride and povidone-iodine; and vitamins and derivatives thereof such as tocopherol, tocopherol acetate, retinoic acid and retinol.

Dispersing and suspending agents are used as aids for the preparation of stable formulations and include, e.g., poligeenan, povidone, and silicon dioxide.

Emollients are agents, preferably non-oily and water-soluble, which soften and soothe the skin, especially skin that has become dry because of excessive loss of water. Such agents are used with pharmaceutical compositions of the present invention which are intended for topical applications, and include, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclo-dextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxy-propylene 15 stearyl ether, propylene glycol, propylene glycol diacetate, sesame oil, and purified water; stabilizers, e.g., calcium saccharate and thymol; surfactants, e.g., lapyrium chloride; laureth 4, ie., α-dodecyl-ω-hydroxy-poly(oxy-1,2-ethanediyl) or polyethylene glycol monododecyl ether.

Emulsifying agents, including emulsifying and stiffening agents and emulsion adjuncts, are used for preparing oil-in-water emulsions when these form the basis of the pharmaceutical compositions of the present invention. Such emulsifying agents include, e.g., non-ionic emulsifiers such as $C_{10}$–$C_{20}$ fatty alcohols and said fatty alcohols condensed with from 2 to 20 moles of ethylene oxide or propylene oxide, ($C_6$–$C_{12}$)alkyl phenols condensed with from 2 to 20 moles of ethylene oxide, mono- and di-$C_{10}$–$C_{20}$ fatty acid esters of ethylene glycol, $C_{10}$–$C_{20}$ fatty acid monoglyceride, diethylene glycol, polyethylene glycols of MW 200 6000, polypropylene glycols of MW 200–3000, and particularly sorbitol, sorbitan, polyoxyethylene sorbitol, polyoxyethylene sorbitan, hydrophilic wax esters, cetostearyl alcohol, oleyl alcohol, lanolin alcohols, cholesterol, mono- and di-glycerides, glyceryl monostearate, polyethylene glycol monostearate, mixed mono- and distearic esters of ethylene glycol and polyoxyethylene glycol, propylene glycol monostearate, and hydroxypropyl cellulose. Emulsifying agents which contain active amine groups may also be used and typically include anionic emulsifiers such as fatty acid soaps, e.g., sodium, potassium and triethanolamine soaps of $C_{10}$–$C_{20}$ fatty acids; alkali metal, ammonium or substituted ammonium ($C_{10}$–$C_{30}$)alkyl sulfates, ($C_{10}$–$C_{30}$)alkyl sulfonates, and ($C_{10}$–$C_{50}$)alkyl ethoxy ether sulfonates. Other suitable emulsifying agents include castor oil and hydrogenated castor oil; lecithin; and polymers of 2-propenoic acid together with polymers of acrylic acid, both cross-linked with allyl ethers of sucrose and/or pentaerythritol, having varying viscosities and identified by product names carbomer 910, 934, 934P, 940, 941, and 1342. Cationic emulsifiers having active amine groups may also be used, including those based on quaternary ammonium, morpholinium and pyridinium compounds. Similarly, amphoteric emulsifiers having active amine groups, such as cocobetaines, lauryl dimethylamine oxide and cocoylimidazoline, may be used. Useful emulsifying and stiffening agents also include cetyl alcohol and sodium stearate; and emulsion adjuncts such as oleic acid, stearic acid, and stearyl alcohol.

Excipients include, e.g., laurocapram and polyethylene glycol monomethyl ether.

Where the pharmaceutical composition of the present invention is to be applied topically, penetration enhancers may be used, which include, e.g., dimethyl isosorbide, diethyl-glycol-monoethylether, 1-dodecyl-azacycloheptan-2-one, and dimethylsulfoxide (DMSO). Such compositions will also typically include ointment bases, e.g., petrolatum, polyethylene glycol, lanolin, and poloxamer, which is a block copolymer of polyoxyethylene and polyoxypropylene, which may also serve as a surfactant or emulsifying agent.

Preservatives are used to protect pharmaceutical compositions of the present invention from degradative attack by ambient microorganisms, and include, e.g., benzalkonium chloride, benzethonium chloride, alkyl esters of p-hydroxybenzoic acid, hydantoin derivatives, cetylpyridinium chloride, monothioglycerol, phenol, phenoxyethanol, methylparagen, imidazolidinyl urea, sodium dehydroacetate, propylparaben, quaternary ammonium compounds, especially polymers such as polixetonium chloride, potassium benzoate, sodium formaldehyde sulfoxylate, sodium propionate, and thimerosal.

Sequestering agents are used to improve the stability of the pharmaceutical compositions of the present invention and include, e.g., the cyclodextrins which are a family of natural cyclic oligosaccharides capable of forming inclusion complexes with a variety of materials, and are of varying ring sizes, those having 6-, 7- and 8-glucose residues in a ring being commonly referred to as α-cyclodextrins, β-cyclodextrins, and γ-cyclodextrins, respectively. Suitable cyclodextrins include, e.g., α-cyclodextrin, β-cyclodextrin, γ-cyclodextrin, δ-cyclodextrin and cationized cyclodextrins.

Solvents which may be used in preparing the pharmaceutical compositions of the present invention include, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water.

Stabilizers which are suitable for use include, e.g., calcium saccharate and thymol.

Stiffening agents are typically used in formulations for topical applications in order to provide desired viscosity and handling characteristics and include, e.g., cetyl esters wax, myristyl alcohol, parafin, synthetic parafin, emulsifying wax, microcrystalline wax, white wax and yellow wax.

Sugars are often used to impart a variety of desired characteristics to the pharmaceutical compositions of the present invention and in order to improve the results obtained, and include, e.g., monosaccharides, disaccharides and polysaccharides such as glucose, xylose, fructose, reose, ribose, pentose, arabinose, allose, tallose, altrose, mannose, galactose, lactose, sucrose, erythrose, glyceraldehyde, or any combination thereof.

Surfactants are employed to provide stability for multi-component pharmaceutical compositions of the present invention, enhance existing properties of those compositions, and bestow desirable new characteristics on said compositions. Surfactants are used as wetting agents, antifoam agents, for reducing the surface tension of water, and as emulsifiers, dispersing agents and penetrants, and include, e.g., lapyrium chloride; laureth 4, i.e., α-dodecyl-ω-hydroxy-poly(oxy-1,2-ethanediyl) or polyethylene glycol monododecyl ether; laureth 9, i.e., a mixture of polyethylene glycol monododecyl ethers averaging about 9 ethylene oxide groups per molecule; monoethanolamine; nonoxynol 4, 9 and 10, i.e., polyethylene glycol mono(p-nonylphenyl) ether; nonoxynol 15, i.e., α-(p-nonylphenyl)-ω-hydroxy-penta-deca(oxyethylene); nonoxynol 30, i.e., α-(p-nonylphenyl)-ω-hydroxytriaconta(oxyethylene); poloxalene, i.e., nonionic polymer of the polyethylenepolypropylene glycol type, MW=approx. 3000; poloxamer, referred to in the discussion of ointment bases further above; polyoxyl 8, 40 and 50 stearate, i.e., poly(oxy-1,2-ethanediyl), α-hydro-co-hydroxy-octa-decanoate; polyoxyl 10 oleyl ether, i.e., poly(oxy-1,2-ethanediyl), α-[(Z)-9-octadecenyl-ω-hydroxy-; polysorbate 20, i.e., sorbitan, mono-dodecanoate, poly(oxy-1,2-ethanediyl); polysorbate 40, i.e., sorbitan, monohexadecanoate, poly(oxy-1,2-ethanediyl); polysorbate 60, i.e., sorbitan, monooctadecanoate, poly(oxy-1,2-ethanediyl); polysorbate 65, i.e., sorbitan, trioctadecanoate, poly(oxy-1,2-ethanediyl); polysorbate 80, i.e., sorbitan, mono-9-monodecenoate, poly(oxy-1,2-ethanediyl); polysorbate 85, i.e., sorbitan, tri-9-octadecenoate, poly(oxy-1,2-ethanediyl); sodium lauryl sulfate; sorbitan monolaurate; sorbitan monooleate; sorbitan monopalmitate; sorbitan monostearate; sorbitan sesquioleate; sorbitan trioleate; and sorbitan tristearate.

The pharmaceutical compositions of the present invention may be prepared using very straightforward methodology which is well understood by the artisan of ordinary skill. Where the pharmaceutical compositions of the present invention are simple aqueous and/or other solvent solutions, the various components of the overall composition are brought together in any practical order, which will be dictated largely by considerations of convenience. Those components having reduced water solubility, but sufficient solubility in the same co-solvent with water, may all be dissolved in said co-solvent, after which the co-solvent solution will be added to the water portion of the carrier whereupon the solutes therein will become dissolved in the water. To aid in this dispersion/solution process, a surfactant may be employed.

Where the pharmaceutical compositions of the present invention are to be in the form of emulsions, the components of the pharmaceutical composition will be brought together in accordance with the following general procedures. The continuous water phase is first heated to a temperature in the range of from about 60° to about 95° C., preferably from about 70° to about 85° C., the choice of which temperature to use being dependent upon the physical and chemical properties of the components which make up the oil-in-water emulsion. Once the continuous water phase has reached its selected temperature, the components of the final composition to be added at this stage are admixed with the water and dispersed therein under high-speed agitation. Next, the temperature of the water is restored to approximately its original level, after which the components of the composition which comprise the next stage are added to the composition mixture under moderate agitation and mixing continues for from about 5 to about 60 minutes, preferably about 10 to about 30 minutes, depending on the components of the first two stages. Thereafter, the composition mixture is passively or actively cooled to from about 20° to about 55° C. for addition of any components in the remaining stages, after which water is added in sufficient quantity to reach its original predetermined concentration in the overall composition.

According to the present invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically acceptable oils, such as olive oil or castor oil, especially in their polyoxyethylated versions. These oil solutions or suspensions may also contain a long-chain alcohol diluent or dispersant, such as Rh, HClX or similar alcohol.

The pharmaceutical compositions of the present invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the present invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

Pharmaceutical compositions within the scope of the present invention include those wherein the therapeutically effective amount of an active ingredient comprising a compound of formula I required for treating or preventing diseases, disorders, and conditions mediated by or associated with modulation of PDE4 activity as described herein, is provided in a dosage form suitable for systemic administration. Such a pharmaceutical composition will contain said active ingredient in suitable liquid form for delivery by: (1) injection or infusion which is intraarterial, intra- or transdermal, subcutaneous, intramuscular, intraspinal, intrathecal, or intravenous, wherein said active ingredient: (a) is contained in solution as a solute; (b) is contained in the discontinuous phase of an emulsion, or the discontinuous phase of an inverse emulsion which inverts upon injection or infusion, said emulsions containing suitable emulsifying agents; or (c) is contained in a suspension as a suspended solid in colloidal or microparticulate form, said suspension containing suitable suspending agents; (2) injection or infusion into suitable body tissues or cavities as a depot, wherein said composition provides storage of said active ingredient and thereafter delayed-, sustained-, and/or controlled-release of said active ingredient for systemic distribution; (3) instillation, inhalation or insufflation into suitable body tissues or cavities of said pharmaceutical composition in suitable solid form, where said active ingredient: (a) is contained in a solid implant composition providing delayed-, sustained-, and/or controlled-release of said active ingredient; (b) is contained in a particulate composition to be inhaled into the lungs; or (c) is contained in a particulate composition to be blown into suitable body tissues or cavities, where said composition optionally provides delayed-, sustained-, and/or controlled-release of said active ingredient; or (4) ingestion of said pharmaceutical composition in suitable solid or liquid form for peroral delivery of said active ingredient, where said active ingredient is contained in a solid dosage form; or (b) is contained in a liquid dosage form.

Particular dosage forms of the above-described pharmaceutical compositions include (1) suppositories as a special type of implant, comprising bases which are solid at room temperature but melt at body temperature, slowly releasing the active ingredient with which they are impregnated into the surrounding tissue of the body, where the active ingredient becomes absorbed and transported to effect systemic administration; (2) solid peroral dosage forms selected from the group consisting of (a) delayed-release oral tablets, capsules, caplets, lozenges, troches, and multiparticulates; (b) enteric-coated tablets and capsules which prevent release and absorption in the stomach to facilitate delivery distal to the stomach of the patient being treated; (c) sustained-release oral tablets, capsules and microparticulates which provide systemic delivery of the active ingredient in a controlled manner up to a 24-hour period; (d) fast-dissolving tablets; (e) encapsulated solutions; (f) an oral paste; (g) a granular form incorporated in or to be incorporated in the food of a patient being treated; and (h) liquid peroral dosage forms selected from the group consisting of solutions, suspensions, emulsions, inverse emulsions, elixirs, extracts, tinctures, and concentrates.

Pharmaceutical compositions within the scope of the present invention include those wherein the therapeutically effective amount of an active ingredient comprising a compound of the present invention required for treating or preventing diseases, disorders, and conditions mediated by or associated with modulation of PDE4 activity as described herein is provided in a dosage form suitable for local administration to a patient being treated, wherein said pharmaceutical composition contains said active ingredient in suitable liquid form for delivering said active ingredient by: (1) injection or infusion into a local site which is intraarterial, intraarticular, intrachondrial, intracostal, intracystic, intra- or transdermal, intrafasicular, intraligamentous, intramedulary, intramuscular, intranasal, intraneural, intraocular, i.e., opthalmic administration, intraosteal, intrapelvic, intrapericardial, intraspinal, intrastemal, intrasynovial, intratarsal, or intrathecal; including components which provide delayed-release, controlled-release, and/or sustained-release of said active ingredient into said local site; where said active ingredient is contained: (a) in solution as a solute; (b) in the discontinuous phase of an emulsion, or the discontinuous phase of an inverse emulsion which inverts upon injection or infusion, said emulsions containing suitable emulsifying agents; or (c) in a suspension as a suspended solid in colloidal or microparticulate form, said suspension containing suitable suspending agents; or (2) injection or infusion as a depot for delivering said active ingredient to said local site; wherein said composition provides storage of said active ingredient and thereafter delayed-, sustained-, and/or controlled-release of said active ingredient into said local site, and wherein said composition also includes components which ensure that said active ingredient has predominantly local activity, with little systemic carryover activity; or wherein said pharmaceutical composition contains said active ingredient in suitable solid form for delivering said inhibitor by: (3) instillation, inhalation or insufflation to said local site, where said active ingredient is contained: (a) in a solid implant composition which is installed in said local site, said composition optionally providing delayed-, sustained-, and/or controlled-release of said active ingredient to said local site; (b) in a particulate composition which is inhaled into a local site comprising the lungs; or (c) in a particulate composition which is blown into a local site, where said composition includes components which will ensure that said active ingredient has predominantly local activity, with insignificant sys temic carryover activity, and optionally provides delayed-, sustained-, and/or controlled release of said active ingredient to said local site. For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

As already mentioned, the compounds of formula I of the present invention may be administered systemically to a patient to be treated as a pharmaceutical composition in suitable liquid form by injection or infusion. There are a number of sites and organ systems in the body of the patient which will allow the properly formulated pharmaceutical composition, once injected or infused, to permeate the entire body and all of the organ system of the patient being treated. An injection is a single dose of the pharmaceutical composition forced, usually by a syringe, into the tissue involved. The most common types of injections are intramuscular, intravenous, and subcutaneous. By contrast, an infusion is the gradual introduction of the pharmaceutical composition into the tissue involved. The most common type of infusion is intravenous. Other types of injection or infusion comprise intraarterial, intra- or transdermal (including subcutaneous), or intraspinal especially intrathecal. In these liquid pharmaceutical compositions, the active ingredient may be contained in solution as the solute. This is the most common and most preferred type of such composition, but requires an active ingredient in a salt form that has reasonably good aqueous solubility. Water (or saline) is by far the most preferred solvent for such compositions. Occasionally supersaturated solutions may be utilized, but these present stability problems that make them impractical for use on an everyday basis.

If it is not possible to obtain a form of some preferred compound that has the requisite degree of aqueous solubility, as may sometimes occur, it is, within the skill of the artisan to prepare an emulsion, which is a dispersion of small globules of one liquid, the discontinuous or internal phase, throughout a second liquid, the continuous or external phase, with which it is immiscible. The two liquids are maintained in an emulsified state by the use of emulsifiers which are pharmaceutically acceptable. Thus, if the active ingredient is a waterinsoluble oil, it can be administered in, an emulsion of which it is the discontinuous phase. Also where the active ingredient is water-insoluble but can be dissolved in a solvent which is immiscible with water, an emulsion can be used. While the active ingredient would most commonly be used as the discontinuous or internal phase of what is referred to as an oil-in-water emulsion, it could also be used as the discontinuous or internal phase of an inverse emulsion, which is commonly referred to as a water-in-oil emulsion. Here the active ingredient is soluble in water and could be administered as a simple aqueous solution. However, inverse emulsions invert upon injection or infusion into an aqueous medium such as the blood, and offer the advantage of providing a more rapid and efficient dispersion of the active ingredient into that aqueous medium than can be obtained using an aqueous solution. Inverse emulsions are prepared by using suitable, pharmaceutically acceptable emulsifying agents well known in the art.

Where the active ingredient has limited water solubility, it may also be administered as a suspended solid in colloidal or microparticulate form in a suspension prepared using suitable, pharmaceutically acceptable suspending agents. The suspended solids containing the active ingredient may also be formulated as delayed-, sustained-, and/or controlled-release compositions.

While systemic administration will most frequently be carried out by injection or infusion of a liquid, there are many situations in which it will be advantageous or even necessary to deliver the active ingredient as a solid. Systemic administration of solids is carried out by instillation, inhalation or insufflation of a pharmaceutical composition in suitable solid form containing the active ingredient. Instillation of the active ingredient may entail installing a solid implant composition into suitable body tissues or cavities. The implant may comprise a matrix of bio-compatible and bio-erodible materials in which particles of a solid active ingredient are dispersed, or in which, possibly, globules or isolated cells of a liquid active ingredient are entrapped. Desirably, the matrix will be broken down and completely absorbed by the body. The composition of the matrix is also preferably selected to provide controlled-, sustained-, and/or delayed release of the active ingredient over extended periods of time, even as much as several months.

The term "implant" most often denotes a solid pharmaceutical composition containing the active ingredient, while the term "depot" usually implies a liquid pharmaceutical composition containing the active ingredient, which is deposited in any suitable body tissues or cavities to form a reservoir or pool which slowly migrates to surrounding tissues and organs and eventually becomes systemically distributed. However, these distinctions are not always rigidly adhered to in the art, and consequently, it is contemplated that there is included within the scope of the present invention liquid implants and solid depots, and even mixed solid and liquid forms for each. Suppositories may be regarded as a type of implant, since they comprise bases which are solid at room temperature but melt at a patient's body temperature, slowly releasing the active ingredient with which they are impregnated into the surrounding tissue of the patient's body, where the active ingredient becomes absorbed and transported to effect systemic administration.

Systemic administration can also be accomplished by inhalation or insufflation of a powder, i.e., particulate composition containing the active ingredient. For example, the active ingredient in powder form may be inhaled into the lungs using conventional devices for aerosolizing particulate formulations. The active ingredient as a particulate formulation may also be administered by insufflation, i.e., blown or otherwise dispersed into suitable body tissues or cavities by simple dusting or using conventional devices for aerosolizing particulate formulations. These particulate compositions may also be formulated to provide delayed-, sustained-, and/or controlled-release of the active ingredient in accordance with well understood principles and known materials.

Other means of systemic administration which may utilize the active ingredients of the present invention in either liquid or solid form include transdermal, intranasal, and opthalmic routes. In particular, transdermal patches prepared in accordance with well known drug delivery technology may be prepared and applied to the skin of a patient to be treated, whereafter the active-agent by reason of its formulated solubility characteristics migrates across the epidermis and info the dermal layers of the patient's skin where it is taken up as part of the general circulation of the patient, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

In the above description of pharmaceutical compositions containing a preferred compound, the equivalent expressions: "administration", "administration of", "administering", and "administering a" have been used with respect to said pharmaceutical compositions. As thus employed, these expressions are intended to mean providing to a patient in need of treatment a pharmaceutical composition of the present invention by any of the routes of administration herein described, wherein the active ingredient is a preferred compound or a prodrug, derivative, or metabolite thereof which is useful in treating a disease, disorder, or condition mediated by or associated with modulation of PDE4 activity in said patient. Accordingly, there is included within the scope of the present invention any other compound which, upon administration to a patient, is capable of directly or indirectly providing a preferred compound. Such compounds are recognized as prodrugs, and a number of established procedures are available for preparing such prodrug forms of the preferred compounds.

The dosage and dose rate of the compounds effective for treating or preventing, a disease, disorder, or condition mediated by or associated with modulation of PDE4 activity, will depend on a variety of factors, such as the nature of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of formula I will be between about 0.1 µg/kg and about 50.0 mg/kg of body weight per day, preferably between about 5.0 µg/kg and about 5.0 mg/kg of body weight per day, more preferably between about 10. 0 µg/kg and about 1.0 mg/kg of body weight per day, and most preferably between about 20.0 µg/kg and about 0. 5 mg/kg of body weight per day of the active ingredient.

Where the dosage form is topically administered to the bronchia and lungs, e.g., by means of a powder inhaler or nebulizer, suitable dosage levels of the compounds will be between about 0.001 µg/kg and about 10.0 mg/kg of body weight per day, preferably between about 0.5 µg/kg and about 0.5 mg/kg of body weight per day, more preferably between about 1.0 µg/kg and about 0.1 mg/kg of body weight per day, and most preferably between about 2.0 µg/kg and about 0.05 mg/kg of body weight per day of the active ingredient.

Using representative body weights of 10 kg and 100 kg in order to illustrate the range of daily oral dosages which might be used as described above, suitable dosage levels of the compounds of formula I will be between about 1.0–10.0 µg and 500.0–5000.0 mg per day, preferably between about 50.0–500.0 µg and 50.0–500.0 mg per day, more preferably between about 100.0–1000.0 µg and 10.0–100.0 mg per day, and most perferably between about 200.0–2000.0 µg and about 5.0–50.0 mg per day of the active ingredient comprising a preferred compound. These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy.

Numerous other factors must also be considered in deciding upon the number of doses per day and the amount of active ingredient per dose that will be administered. Not the least important of such other factors is the individual respsonse of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered, each day, each dose containing from about 50.0 µg to about 10.0 mg of active ingredient.

The invention furthermore relates to medicaments comprising at least one compound of the formula I and/or its pharmaceutically usable derivatives, solvates and stereoisomers, including mixtures thereof in all ratios, and optionally excipients and/or assistants.

The invention furthermore relates to medicaments comprising at least one compound of the formula I and/or its pharmaceutically usable derivatives, solvates and stereoisomers, including mixtures thereof in all ratios, and at least one further medicament active ingredient.

The invention also relates to a set (kit) consisting of separate packs of (a) an effective amount of a compound of the formula I and/or its pharmaceutically usable derivatives, solvates and stereoisomers, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or its pharmaceutically usable derivatives, solvates and stereoisomers, including mixtures thereof in all ratios, and an effective amount of a further medicament active ingredient in dissolved or lyophilised form.

All temperatures hereinabove and hereinbelow are given in ° C. In the examples which follow, "usual work-up" means: if required, water is added; if required, the pH is brought to between 2 and 10, depending on the constitution of the end product; the mixture is extracted with ethyl acetate or dichloromethane and separated; the organic phase is dried over sodium sulfate and evaporated; and the residue is purified by chromatography on silica gel and/or by crystallization.

Mass spectrometry (MS): EI (electron impact ionization) M+ FAB (fast atom bombardment)(M+H)+

EXAMPLE 1

1.1 A solution of 70 ml 3-chlorocarbonyl-propionic acid methyl ester in 100 ml dichloromethane is added to a suspension of 80.0 g of AlCl$_3$ in 300 ml dichloromethane at 20–25°. At 0° a solution of 85.0 g 1,2-diethoxybenzene in 100 ml dichloromethane is added. The solution is tirred for 14 hours at room temperature. Work-up is as usual, yielding 122.2 g of 4-(3,4-diethoxy-phenyl)-4-oxo-butyric acid methyl ester ("AA"), m.p. 84–85°.

1.2 A mixture of 122,2 g "AA" and 40 ml hydrazinium hydroxide in 500 ml acetic acid is refluxed for 3 hours. Work-up is as usual, yielding 105.9 g of 6-(3,4-diethoxy-phenyl)-4,5-dihydro-2H-pyridazin-3-one ("AB"), m.p. 142–143°.

1.3 7.0 g LiAlH$_4$ in 200 ml THF is added to a suspension of 45.0 g "AB" in 300 ml THF at 0–5° under N$_2$-atmosphere. The mixture is stirred for 1 hour at room temperature. Work-up is as usual, yielding 42.3 g of 3-(3,4-diethoxy-phenyl)-1,4,5,6-tetrahydro-pyridazine ("AC"), m.p. 77-78°.

1.4 11.0 g in 100 ml methylene chloride is added to a solution of 14.1 g "AC" and 5 ml pyridine in 200 ml methylene chloride at 0°. The solution is stirred for 16 hours at room temperature.

Work-up is as usual, yielding 17.1 g of [3-(3,4-diethoxy-phenyl)-5,6-dihydro-4H-pyridazine-1-yl]-(3-nitro-phenyl)-methanone ("AD"), m.p. 119–120°.

1.5 17.0 g "AD" are hydrogenated in conventional manner. Work-up is as usual, yielding 14.1 g of [3-(3,4-diethoxy-phenyl)-5,6-dihydro-4H-pyridazine-1-yl]-(3-amino-phenyl)-methanone ("AE"), m.p. 162–163°.

1.6 147 mg sodium nitrite in 5 ml water is added to a suspension of 1.5 ml HCl (25%) and 709 mg "AE" in 30 ml water at −2 to 0° and the mixture stirred for 1 hour. 128 mg malonodinitrile in 5 ml water is added and the mixture is stirred for 2 hours at room temperature, pH is adjusted with a solution of sodium acetate in water to a value of 5. The precipitate is collected, washed with water and few ethanol and dried at 50° for 16 hours. One equivalent of 0.5 M KOH/methanol is added. The potassium salt crystallizes by addition of iso-propanol.

Yield: 300 mg 2-[(3-[(1-[3-(3,4-diethoxy-phenyl)-5,6-dihydro-4H-pyridazin-1-yl]-methanoyl}phenyl)-hydrazono]-malonitrile, potassium salt

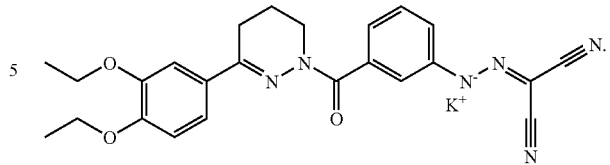

Analogously, by reacting malonodinitrile with
[3-(3-ethoxy-4-methoxy-phenyl)-5,6-dihydro-4H-pyridazine-1-yl]-(4-amino-2-chloro-phenyl)-methanone,
[3-(3-ethoxy-4-methoxy-phenyl)5,6-dihydro-4H-pyridazine-1-yl]-(4-amino-phenyl)-methanone,
[3-(3-ethoxy-4-methoxy-phenyl)-5,6-dihydro-4H-pyridazine-1-yl]-(4-amino-2-fluoro-phenyl)-methanone,
[3-(3-benzyloxy-4-methoxy-phenyl)-5,6-dihydro-4H-pyridazine-1-yl]-(4-amino-phenyl)-methanone,
[3-(3,4-difluoro-phenyl)-5,6-dihydro-4H-pyridazine-1-yl]-(4-amino-phenyl)-methanone, potassium salt;
[3-(4-ethyl-phenyl)-5,6-dihydro-4H-pyridazine-1-yl]-(4-amino-phenyl)-methanone,
[3-(3-propoxy-4-methoxy-phenyl)-5,6-dihydro-4H-pyridazine-1-yl]-(4-amino-phenyl)-methanone,
[3-(3-isopropoxy-4-methoxy-phenyl)-5,6-dihydro-4H-pyridazine-1-yl]-(4-amino-phenyl)-methanone, the following compounds are obtained
2-[(3-chloro-4-{1-[3-(3-ethoxy-4-methoxy-phenyl)-5,6-dihydro-4H-pyridazine-1-yl]-methanoyl}-phenyl)-hydrazono]-malonitrile, potassium salt;
2-[(4-{1-[3-(3-ethoxy-4-methoxy-phenyl)-5,6-dihydro-4H-pyridazine-1-yl]-methanoyl}-phenyl)-hydrazono]-malonitrile, potassium salt;
2-[(3-fluoro-4-{1-[3-(3-ethoxy-4-methoxy-phenyl)-5,6-dihydro-4H-pyridazine-1-yl]-methanoyl}phenyl)-hydrazono]-malonitrile, potassium salt;
2-[(4-{1-[3-(3-benzyloxy-4-methoxy-phenyl)-5,6-dihydro-4H-pyridazine-1-yl]-methanoyl}phenyl)-hydrazono]-malonitrile, potassium salt;
2-[(4-{1-[3-(3,4-difluoro-phenyl)-5,6-dihydro-4H-pyridazine-1-yl]-methanoyl}-phenyl)-hydrazono]-malonitrile, potassium salt;
2-[(4-[(1-[3-(4-ethyl-phenyl)-5,6-dihydro-4H-pyridazine-1-yl]-methanoyl}-phenyl)-hydrazono]-malonitrile, potassium salt;
2-[(4-{1-[3-(3-propoxy-4-methoxy-phenyl)-5,6-dihydro-4H-pyridazine-1-yl]-methanoyl}-phenyl)-hydrazono]-malonitrile, potassium salt;
2-[(4-{1-[3-(3-isopropoxy-4-methoxy-phenyl)-5,6-dihydro-4H-pyridazine-1-yl]-methanoyl}-phenyl)-hydrazono]-malonitrile, potassium salt.

EXAMPLE 2

2.1 Isovanilin is reacted with iodoethane in acetonitrile and potassium carbonate.

Work-up is as usual, yielding 3-ethoxy-4-methoxy-benzaldehyde ("BA").

2.2 "BA" is reacted with morpholine, sodium cyanide and p-tolyl-sulfonic acid in tetrahydrofurane (THF) to yield (3-ethoxy-4-methoxy-phenyl)-morpholin-4-yl-acetonitrile ("BB").

2.3 "BB" is reacted with methyl methacrylate in sodium methanolate to yield 4-cyano-4-(3-ethoxy-4-methoxy-phenyl)-4-morpholin-4-yl-butyric acid methyl ester ("BC").

2.4 "BC" is reacted with hydrazinium hydroxide in ethanol to yield 6-(3-ethoxy-4-methoxy-phenyl)4,5-dihydro-2H-pyridazin-3-one ("BD").

2.5 Analogously to example 1.3 "BC" is converted to 3-(3-ethoxy-4-methoxy-phenyl)-1,4,5,6-tetrahydro-pyridazine ("BE").

2.6 Analogously to example 1.4 "BE" is reacted with 2-chloro-4-nitro-benzoylchloride to yield [3-(3-ethoxy-4-methoxy-phenyl)-5,6-dihydro-4H-pyridazine-1-yl]-(2-chloro-4-nitro-phenyl)-methanone ("BF").

2.7 "BF" is converted to [3-(3-ethoxy-4-methoxy-phenyl)-5,6-dihydro-4H-pyridazine-1-yl]-(2-chloro-4-amino-phenyl)-methanone ("BG") by hydrogenation with Raney-nickel in THF.

2.8 Analogously to example 1.6 "BF" is reacted with malonodinitrile to yield 2-[(3-chloro-4-{1–13-(3,4-diethoxy-phenyl)-5,6-dihydro-4H-pyridazin-1-yl]-methanoyl}-phenyl)-hydrazono]-malonitrile, potassium salt.

EXAMPLE 3

A solution of 500 mg 2-[(3-fluoro-4-{1-[3-(3-ethoxy-4-methoxy-phenyl)-5,6-dihydro-4H-pyridazine-1-yl]-methanoyl}-phenyl)-hydrazono]-malonitrile, 66 mg ammonium chloride, 81 mg sodium azide and a catalytic amount of lithium chloride in 4 ml DMF is stirred for 24 hours at 120°. After usual work-up, the dried crystals are resolved in methanol.

An equivalent amount of KOH in methanol is added. The solvent is removed and ethyl acetate/diethylether is added to the residue.

Yield: 460 mg [(4-{1-[3-(3-ethoxy-4-methoxy-phenyl)-5,6-dihydro-4H-pyridazine-1-yl]-methanoyl}-3-fluoro-phenyl)-hydrazono]-2-(1H-tetrazol-5-yl)-acetonitrile, potassium salt

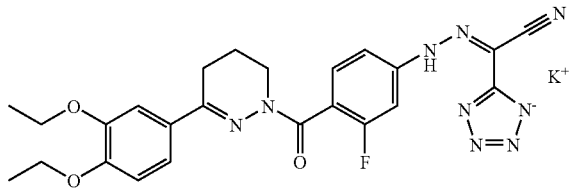

Analogously, the following compounds are obtained
[(3-{1-[3-(3,4-diethoxy-phenyl)-5,6-dihydro-4H-pyridazin-1-yl]-methanoyl}-phenyl)-hydrazono]-2-(1H-tetrazol-5-yl)-acetonitrile,
[(3-chloro-4-{1-[3-(3-ethoxy-4-methoxy-phenyl)-5,6-dihydro-4H-pyridazine-1-yl]-methanoyl}-phenyl)-hydrazono]-2-(1H-tetrazol-5-yl)-acetonitrile,
[(4-{1-[3-(3-ethoxy-4-methoxy-phenyl)-5,6-dihydro-4H-pyridazine-1-yl]-methanoyl}-phenyl)-hydrazono]-2-(1H-tetrazol-5-yl)-acetonitrile,
[(4-{1-[3-(3-benzyloxy-4-methoxy-phenyl)-5,6-dihydro-4H-pyridazine-1-yl]-methanoyl}-phenyl)-hydrazono]-2-(1H-tetrazol-5-yl)-acetonitrile,
[(4-{1-[3-(3,4-difluoro-phenyl)-5,6-dihydro-4H-pyridazine-1-yl]-methanoyl}-phenyl)-hydrazono]-2-(1H-tetrazol-5-yl)-acetonitrile,
[(4-{1-[3-(4-ethyl-phenyl)-5,6-dihydro-4H-pyridazine-1-yl]-methanoyl}-phenyl)-hydrazono]-2-(1H-tetrazol-5-yl)-acetonitrile,
[(4-{1-[3-(3-propoxy-4-methoxy-phenyl)-5,6-dihydro-4H-pyridazine-1-yl]-methanoyl}-phenyl)-hydrazono]-2-(1H-tetrazol-5-yl)-acetonitrile,
[(4-{1-[3-(3-isopropoxy-4-methoxy-phenyl)-5,6-dihydro-4H-pyridazine-1-yl]-methanoyl}-phenyl)-hydrazono]-2-(1H-tetrazol-5-yl)-acetonitrile.

EXAMPLE 4

Analogously to example 1 or 2, the following compounds of formula I-A (Table I) are obtained

TABLE I

| nr. | $R^1$ | $R^2$ | $R^3$ | $R^{3'}$ | $R^6$ | $R^7$ | remarks |
|---|---|---|---|---|---|---|---|
| I-A-1 | OMe | OMe | F | H | H | H | |
| I-A-2 | OMe | OMe | Cl | H | H | H | |
| I-A-3 | OMe | OMe | H | H | H | H | |
| I-A-4 | OMe | OMe | H | F | H | H | |
| I-A-5 | OMe | OMe | H | Cl | H | Cl | |
| I-A-6 | OMe | OEt | F | H | H | H | |
| I-A-7 | OMe | OEt | Cl | H | H | H | |
| I-A-8 | OMe | OEt | H | H | H | H | |
| I-A-9 | OMe | OEt | H | F | H | H | |
| I-A-10 | OMe | OEt | H | Cl | H | Cl | |
| I-A-11 | OMe | OCp | F | H | H | H | |
| I-A-12 | OMe | OCp | Cl | H | H | H | |
| I-A-13 | OMe | OCp | H | H | H | H | |
| I-A-14 | OMe | OCp | H | F | H | H | |
| I-A-15 | OMe | OCp | H | Cl | H | Cl | |
| I-A-16 | OMe | $OCF_2$ | F | H | H | H | |
| I-A-17 | OMe | $OCF_2$ | Cl | H | H | H | |
| I-A-18 | OMe | $OCF_2$ | H | H | H | H | |
| I-A-19 | OMe | $OCF_2$ | H | F | H | H | |
| I-A-20 | OMe | $OCF_2$ | H | Cl | H | Cl | |

OMe = methoxy;
OEt = ethoxy;
OCp = cyclopentoxy

EXAMPLE 5

Analogously to example 1 or 2, the following compounds of formula I-B (Table II) are obtained

TABLE II

| nr. | $R^1$ | $R^2$ | $R^3$ | $R^{3'}$ | $R^6$ | $R^7$ | remarks |
|---|---|---|---|---|---|---|---|
| I-B-1 | OMe | OMe | H | H | H | H | |
| I-B-2 | OMe | OMe | Cl | H | H | H | |
| I-B-3 | OMe | OMe | H | H | F | H | |
| I-B-4 | OMe | OMe | H | H | Cl | H | |
| I-B-5 | OMe | OMe | H | F | H | H | |

TABLE II-continued

I-B

Structure: R¹, R² on left phenyl; pyridazine-N-N-C(=O)-phenyl(R³,R³',R⁶,R⁷)-NH-N=C(CN)(CN)

| nr. | R¹ | R² | R³ | R³' | R⁶ | R⁷ | remarks |
|---|---|---|---|---|---|---|---|
| I-B-6 | OMe | OMe | H | Cl | H | H | |
| I-B-7 | OMe | OMe | H | OMe | H | H | |
| I-B-8 | OMe | OEt | H | H | H | H | |
| I-B-9 | OMe | OEt | Cl | H | H | H | |
| I-B-10 | OMe | OEt | H | H | F | H | |
| I-B-11 | OMe | OEt | H | H | Cl | H | |
| I-B-12 | OMe | OEt | H | F | H | H | |
| I-B-13 | OMe | OEt | H | Cl | H | H | |
| I-B-14 | OMe | OEt | H | OMe | H | H | |
| I-B-15 | OMe | OCp | H | H | H | H | |
| I-B-16 | OMe | OCp | Cl | H | H | H | |
| I-B-17 | OMe | OCp | H | H | F | H | |
| I-B-18 | OMe | OCp | H | H | Cl | H | |
| I-B-19 | OMe | OCp | H | F | H | H | |
| I-B-20 | OMe | OCp | H | Cl | H | H | |
| I-B-21 | OMe | OCp | H | OMe | H | H | |
| I-B-22 | OMe | OCF₂ | H | H | H | H | |
| I-B-23 | OMe | OCF₂ | Cl | H | H | H | |
| I-B-24 | OMe | OCF₂ | H | H | F | H | |
| I-B-25 | OMe | OCF₂ | H | H | Cl | H | |
| I-B-26 | OMe | OCF₂ | H | F | H | H | |
| I-B-27 | OMe | OCF₂ | H | Cl | H | H | |
| I-B-28 | OMe | OCF₂ | H | OMe | H | H | |

OMe = methoxy;
OEt = ethoxy;
OCp = cyclopentoxy

EXAMPLE 6

Analogously to example 3, the following compounds of formula I-C (Table III) are obtained

TABLE III

I-C

| nr. | R¹ | R² | R³ | R³' | R⁶ | R⁷ | remarks |
|---|---|---|---|---|---|---|---|
| I-C-1 | OMe | OMe | F | H | H | H | |
| I-C-2 | OMe | OMe | Cl | H | H | H | |
| I-C-3 | OMe | OMe | H | H | H | H | |
| I-C-4 | OMe | OMe | H | F | H | H | |
| I-C-5 | OMe | OMe | H | Cl | H | Cl | |
| I-C-6 | OMe | OEt | F | H | H | H | |
| I-C-7 | OMe | OEt | Cl | H | H | H | |
| I-C-8 | OMe | OEt | H | H | H | H | |
| I-C-9 | OMe | OEt | H | F | H | H | |
| I-C-10 | OMe | OEt | H | Cl | H | Cl | |
| I-C-11 | OMe | OCp | F | H | H | H | |

TABLE III-continued

I-C

| nr. | R¹ | R² | R³ | R³' | R⁶ | R⁷ | remarks |
|---|---|---|---|---|---|---|---|
| I-C-12 | OMe | OCp | Cl | H | H | H | |
| I-C-13 | OMe | OCp | H | H | H | H | |
| I-C-14 | OMe | OCp | H | F | H | H | |
| I-C-15 | OMe | OCp | H | Cl | H | Cl | |
| I-C-16 | OMe | OCF₂ | F | H | H | H | |
| I-C-17 | OMe | OCF₂ | Cl | H | H | H | |
| I-C-18 | OMe | OCF₂ | H | H | H | H | |
| I-C-19 | OMe | OCF₂ | H | F | H | H | |
| I-C-20 | OMe | OCF₂ | H | Cl | H | Cl | |

OMe = methoxy;
OEt = ethoxy;
OCp = cyclopentoxy

EXAMPLE 7

Analogously to example 3, the following compounds of formula I-D (Table IV) are obtained

TABLE IV

I-D

| nr. | R¹ | R² | R³ | R³' | R⁶ | R⁷ | remarks |
|---|---|---|---|---|---|---|---|
| I-D-1 | OMe | OMe | H | H | H | H | |
| I-D-2 | OMe | OMe | Cl | H | H | H | |
| I-D-3 | OMe | OMe | H | H | F | H | |
| I-D-4 | OMe | OMe | H | H | Cl | H | |
| I-D-5 | OMe | OMe | H | F | H | H | |
| I-D-6 | OMe | OMe | H | Cl | H | H | |
| I-D-7 | OMe | OMe | H | OMe | H | H | |
| I-D-8 | OMe | OEt | H | H | H | H | |
| I-D-9 | OMe | OEt | Cl | H | H | H | |
| I-D-10 | OMe | OEt | H | H | F | H | |
| I-D-11 | OMe | OEt | H | H | Cl | H | |
| I-D-12 | OMe | OEt | H | F | H | H | |
| I-D-13 | OMe | OEt | H | Cl | H | H | |
| I-D-14 | OMe | OEt | H | OMe | H | H | |
| I-D-15 | OMe | OCp | H | H | H | H | |
| I-D-16 | OMe | OCp | Cl | H | H | H | |
| I-D-17 | OMe | OCp | H | H | F | H | |
| I-D-18 | OMe | OCp | H | H | Cl | H | |
| I-D-19 | OMe | OCp | H | F | H | H | |
| I-D-20 | OMe | OCp | H | Cl | H | H | |
| I-D-21 | OMe | OCp | H | OMe | H | H | |
| I-D-22 | OMe | OCF₂ | H | H | H | H | |
| I-D-23 | OMe | OCF₂ | Cl | H | H | H | |
| I-D-24 | OMe | OCF₂ | H | H | F | H | |

TABLE IV-continued

| nr. | R¹ | R² | R³ | R³' | R⁶ | R⁷ | remarks |
|---|---|---|---|---|---|---|---|
| I-D-25 | OMe | OCF₂ | H | H | Cl | H | |
| I-D-26 | OMe | OCF₂ | H | F | H | H | |
| I-D-27 | OMe | OCF₂ | H | Cl | H | H | |
| I-D-28 | OMe | OCF₂ | H | OMe | H | H | |

OMe = methoxy;
OEt = ethoxy;
OCp = cyclopentoxy

EXAMPLE I

Effect of the Compounds of Formula I on T-cell Proliferation

Peripheral blood mononuclear cells (PBMC) are isolated from the blood of healthy donors by the Lymphoprep gradient method. 200000 PBMC/well are cultured in RPMI 1640 culture medium containing 5% heat inactivated human serum (AB pool) for 5 days at 37° C. and 10% $CO_2$ in 96 well flat bottom microtiter plates. The T cells within the PBMC preparation are selectively stimulated with an monoclonal antibody to CD3. Cultures are set up as triplicates including a control group receiving no treatment.

The compounds of formula I are dissolved in DMSO at $10^{-2}$ M and diluted in culture medium. Control cultures are treated with DMSO equivalent to the inhibitor concentration. 18 hrs before the end of the assay, ³H-thymidine is added to the cultures. The incorporation of radioactivity into the cells is then measured in a beta-counter.

The data of at least three independent experiments are calculated as percent inhibition of the control (mean±SEM) without inhibitor. From this data the IC-50 value is determined.

Results:

The compounds of formula I afford a marked reduction of T-cell proliferation.

EXAMPLE II

Effect of the Compounds of Formula I on Cytokine Production in Human Peripheral Blood Monocytic Cells Peripheral blood mononuclear cells (PBMC) are isolated from the blood of healthy donors by the Lymphoprep gradient method. 200000 PBMC/well are cultured in RPMI1640 culture medium containing 5% heat inactivated human serum (AB pool), at 37° C. and 10% $CO_2$ in 96 well flat bottom microtiter plates. Cultures are set up as triplicates including a control group. Solutions of the compounds of formula I are prepared in DMSO at $10^{-2}$ M and diluted in culture medium. Control cultures are treated with concentrations of DMSO equivalent to the inhibitor concentrations.

The culture supernatants of three independent experiments are pooled and cytokine activity in the supernatant is measured with commercially available ELISA test kits.

The data are calculated as percent inhibition/stimulation of the control without the compound and the $IC_{50}$ value or $EC_{50}$ value in case of stimulation is determined thereof.

Result

The compounds of formula I afford a marked reduction in the release of IL-2, IFN-γ, TNF-α and IL-12. The immunosuppressant cytokine IL-10, however, is stimulated.

EXAMPLE III

Effect of the Compounds of Formula I on Experimental Myocardial Infarction in Rats The compounds of formula I, administered intraperitoneally with 1, 3, and 10 mg/kg, 1 hour before reversible occlusion of the left coronary artery in rats cause a significant dose dependent reduction of infarct size. In correspondence with this protection, a reduction of plasma TNF-α levels is observed, as measured by ELISA.

EXAMPLE IV

Effect of the Compounds of Formula I on Experimental Myocardial Infarction in Rabbits There is a cardioprotective effect by PDE4 inhibition in anaesthetised rabbits subjected to 30 minutes of coronary artery occlusion (side branch of the ramus circumflexus of the left coronary artery) followed by 120 minutes of reperfusion. Compounds of formula I applied prior to the coronary occlusion, reduce infarct size as compared with placebo treatment. The areas at risk are comparable between verum and placebo groups. The cardioprotective effect cannot be attributed to favorable hemodynamic effects, since heart rate and mean aortic pressure remain constant throughout the experimental protocol.

The following examples relate to pharmaceutical preparations:

EXAMPLE A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution of 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water is prepared. The solution is adjusted to pH 6.8, made up to 1 and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F

Coated Tablets

Analogously to Example E, tablets are pressed and are then coated in a customary manner with a coating of sucrose, potato starch, talc, tragacanth and colourant.

EXAMPLE G

Capsules 2 kg of active compound of the formula I are filled into hard gelatin capsules in a customary manner such that each capsule contains 20 mg of the active compound.

EXAMPLE H

Ampoules

A solution of 1 kg of active compound of the formula I in 60 l of double-distilled water is sterile-filtered, filled into ampoules, lyophilized under sterile conditions and aseptically sealed. Each ampoule contains 10 mg of active compound.

The invention claimed is:

1. A compound of the formula I

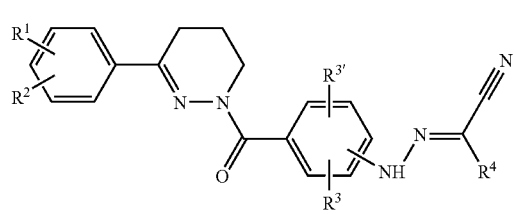

I in which $R^1$, $R^2$ in each case independently of one another are H, OH, $OR^5$, $-SR^5$, $-SOR^5$, $-SO_2R^5$ or Hal, $R^1$ and $R^2$ together are also $-OCH_2O-$ or $-OCH_2CH_2O-$, $R^3$, $R^{3'}$ in each case independently of one another are H, $R^5$, OH, $OR^5$, $NH_2$, $NHR^5$, $NAA'$, $NHCOR^5$, $NHCOOR^5$, Hal, COOH, $COOR^5$, $CONH_2$, $CONHR^5$ or $CONR^5A'$, $R^4$ is CN or

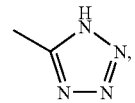

$R^5$ is A or cycloalkyl with 3 to 6 C-atoms, which can be substituted by 1 to 5 F and/or Cl atoms, or $-(CH_2)_n-Ar$, A, A' in each case independently of one another are alkyl with 1 to 10 C-atoms or are alkenyl with 2 to 8 C-atoms, which can be substituted by 1 to 5 F and/or Cl atoms, A and A' together are also cycloalkyl or cycloalkylene with 3 to 7 C-atoms, wherein one $CH_2$ group can be replaced by O, NH, NA, NCOA or NCOOA, Ar is phenyl, n is 0, 1 or 2, Hal is F, Cl, Br or I or a pharmaceutically acceptable salt, or a stereoisomer thereof.

2. A compound according to claim 1 in which $R^1$, $R^2$ in each case independently of one another are OA, A, OAr or Hal;

or a pharmaceutically acceptable salt, or a stereoisomer thereof.

3. A compound according to claim 1 in which $R^1$, $R^2$ in each case independently of one another are OA, A, OAr or Hal, and $R^3$ is H, Hal or OA;

or a pharmaceutically acceptable salt, or a stereoisomer thereof.

4. A compound according to claim 1 in which $R^1$, $R^2$ in each case independently of one another are OA, A, OAr or Hal, $R^3$ is H, Hal or OA, and $R^5$ is A;

or a pharmaceutically acceptable salt, or a stereoisomer thereof.

5. A compound according to claim 1 in which $R^1$, $R^2$ in each case independently of one another are OA, A, OAr or Hal, $R^3$ is H, Hal or OA, $R^5$ is A, A is alkyl with 1 to 6 C-atoms;

or a pharmaceutically acceptable salt, or a stereoisomer thereof.

6. A compound according to claim 1 in which $R^1$, $R^2$ in each case independently of one another are OA, A, OAr or Hal, $R^3$, $R^{3'}$ in each case independently of one another are H, Hal or OA, $R^5$ is A, A is alkyl with 1 to 6 C-atoms, and Ar is phenyl;

or a pharmaceutically acceptable salt, or a stereoisomer thereof.

7. A compound according to claim 1, which is
a) 2-[(3-chloro-4-{1-[3-(3-ethoxy-4-methoxy-phenyl)-5,6-dihydro-4H-pyridazine-1-yl]-methanoyl}-phenyl)-hydrazono]-malonitrile,
b) 2-[(4-{1-[3-(3-ethoxy-4-methoxy-phenyl)-5,6-dihydro-4H-pyridazine-1-yl]-methanoyl}-phenyl)-hydrazono]-malonitrile,
c) 2-[(3-fluoro-4-{1-[3-(3-ethoxy-4-methoxy-phenyl)-5,6-dihydro-4H-pyridazine-1-yl]-methanoyl}-phenyl)-hydrazono]-malonitrile,
d) 2-[(4-{1-[3-(3-benzyloxy-4-methoxy-phenyl)-5,6-dihydro-4H-pyridazine-1-yl]-methanoyl}-phenyl)-hydrazono]-malonitrile,
e) 2-[(4-{1-[3-(3,4-difluoro-phenyl)-5,6-dihydro-4H-pyridazine-1-yl]-methanoyl}-phenyl)-hydrazono]-malonitrile,
f) [(4-{1-[3-(3-ethoxy-4-methoxy-phenyl)-5,6-dihydro-4H-pyridazine-1-yl]-methanoyl}-3-fluoro-phenyl)-hydrazono]-2-(1H-tetrazol-5-yl)-acetonitrile,
g) 2-[(4-{1-[3-(4-ethyl-phenyl)-5,6-dihydro-4H-pyridazine-1-yl]-methanoyl}-phenyl)-hydrazono]-malonitrile,
h) 2-[(4-{1-[3-(3-propoxy-4-methoxy-phenyl)-5,6-dihydro-4H-pyridazine-1-yl]-methanoyl}-phenyl)-hydrazono]-malonitrile, or
i) 2-[(4-{1-[3-(3-isopropoxy-4-methoxy-phenyl)-5,6-dihydro-4H-pyridazine-1-yl-methanoyl}-phenyl)-hydrazono]-malonitrile,
or a pharmaceutically acceptable salt, or a stereoisomer thereof.

8. A process for the preparing a compound of claim 1, wherein $R^4$ is cyano, or a salt thereof, comprising
a) a compound of the formula II

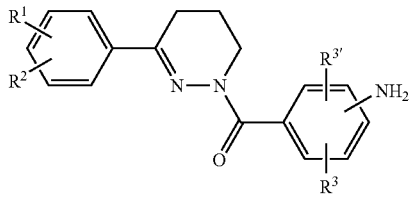

in which
$R^1$, $R^2$, $R^3$, $R^{3'}$ have the meanings indicated in claim 1, with malodinitrile, or
b) in a compound of the formula I, a radical $R^4$ is converted into another radical $R^4$ by converting a cyano group to a tetrazol group, and/or in that a basic compound of the formula I is converted into one of its salts by treatment with an acid.

9. A pharmaceutical composition comprising at least one compound according to claim 1 or a pharmaceutically acceptable salt, or a stereoisomer thereof and one or more excipients and/or adjuvants.

10. A compound of formula I—I

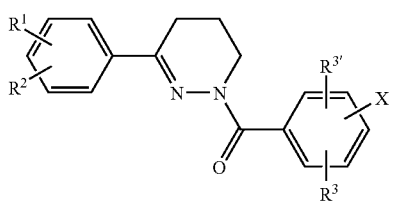

in which
$R^1$, $R^2$ in each case independently of one another are H, OH, $OR^5$, —$SR^5$, —$SOR^5$, —$SO_2R^5$ or Hal, $R^1$ and $R^2$ together are alternatively —$OCH_2O$— or —$OCH_2C_2O$—,
$R^3$, $R^{3'}$ in each case independently of one another are $R^5$, OH, $OR^5$, $NH_2$, $NHR^5$, $NAA'$, $NHCOR^5$, $NHCOOR^5$, Hal, COOH, $COOR^5$, $CONH_2$, $CONHR^5$ or $CONR^5A'$,
$R^5$ is A or cycloalkyl with 3 to 6 C-atoms, which can be substituted by 1 to 5 F and/or Cl atoms,
or —$(CH_2)_n$-Ar,
X $NO_2$ or $NH_2$,
A, A' in each case independently of one another are alkyl with 1 to 10 C-atoms or are alkenyl with 2 to 8 C-atoms, which can be substituted by 1 to 5 F and/or Cl atoms,
A and A' together are also cycloalkyl or cycloalkylene with 3 to 7 C-atoms, wherein one $CH_2$ group can be replaced by O, NH, NA, NCOA or NCOOA,
Ar is phenyl,
n is 0, 1 or 2, and
Hal is F, Cl, Br or I,
or a salt thereof.

11. A compound of formula I

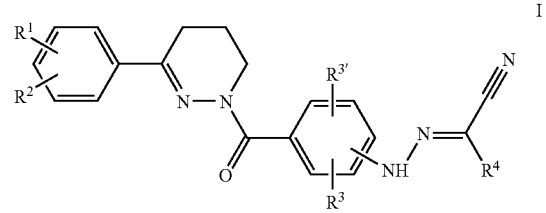

in which
$R^1$, $R^2$ in each case independently of one another are H, OH, $OR^5$, —$SR^5$, —$SOR^5$, —$SO_2R^5$ or Hal,
$R^1$ and $R^2$ together are also —$OCH_2O$— or —$OCH_2CH_2O$—,
$R^3$, $R^{3'}$ in each case independently of one another are H, $R^5$, OH, $OR^5$, $NH_2$, $NHR^5$, $NAA'$, $NHCOR^5$, $NHCOOR^5$, Hal, COOH, $COOR^5$, $CONH_2$, $CONHR^5$ or $CONR^5A'$,
$R^4$ is CN or

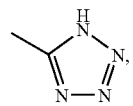

$R^5$ is A or cycloalkyl with 3 to 6 C-atoms, which can be substituted by 1 to 5 F and/or Cl atoms,
or —$(CH_2)_n$—Ar,
A, A' in each case independently of one another are alkyl with 1 to 10 C-atoms or are alkenyl with 2 to 8 C-atoms, which can be substituted by 1 to 5 F and/or Cl atoms,
A and A' together are also cycloalkyl or cycloalkylene with 3 to 7 C-atoms, wherein one $CH_2$ group can be replaced by O, NH, NA, NCOA or NCOOA,
Ar is phenyl,
n is 0, 1 or 2,
Hal is F, Cl, Br or I
or a pharmaceutically acceptable salt, prodrug, solvate or a stereoisomer thereof.

12. A compound according to claim 11, which is in the form of a solvate.

* * * * *

UNITED STATES PATENT AND TRADEMARK OFFICE
CERTIFICATE OF CORRECTION

PATENT NO.       : 7,141,572 B2                                    Page 1 of 1
APPLICATION NO.  : 10/494631
DATED            : November 28, 2006
INVENTOR(S)      : Hans-Michael Eggenweiler It is certified that error appears in the above-identified patent and that said Letters Patent is hereby corrected as shown below:

Column 53, line 3, reads "4H" should read -- 4*H* --
Column 53, line 6, reads "4H" should read -- 4*H* --
Column 53, line 9 reads "4H" should read -- 4*H* --
Column 53, line 12, reads "4H" should read -- 4*H* --
Column 53, line 14, reads "4H" should read -- 4*H* --
Column 53, line 17, reads "4H" should read -- 4*H* --
Column 53, line 18, reads "4H" should read -- 4*H* --
Column 53, line 19, reads "4H" should read -- 4*H* --
Column 53, line 23, reads "4H" should read -- 4*H* --
Column 53, line 26, reads "4H" should read -- 4*H* --
Column 53, line 30, reads "for the preparing" should read -- for preparing --
Column 53, line 32, reads "a compound of the formula" should read -- reacting a compound of formula --
Column 53, line 48, begin new line before "and/or"
Column 53, line 48, reads "and/or in that a" should read -- and/or a --
Column 53, line 49, reads "of the formula I" should read -- of formula I --
Column 53, line 53, reads "stercoisomer" should read -- stereoisomer --
Column 54, line 1, reads "-OCH$_2$O-or" should read -- -OCH$_2$O- or --

Signed and Sealed this

Twenty-ninth Day of May, 2007

JON W. DUDAS
*Director of the United States Patent and Trademark Office*